(12) United States Patent
Schneider et al.

(10) Patent No.: US 9,062,332 B2
(45) Date of Patent: Jun. 23, 2015

(54) PROCESS FOR THE FERMENTATIVE PREPARATION OF SULPHUR-CONTAINING AMINO ACIDS

(75) Inventors: Frank Schneider, Halle (DE); Stella Molck, Bielefeld (DE); Brigitte Bathe, Salzkotten (DE)

(73) Assignee: EVONIK DEGUSSA GMBH, Essen (DE)

( * ) Notice: Subject to any disclaimer, the term of this patent is extended or adjusted under 35 U.S.C. 154(b) by 141 days.

(21) Appl. No.: 13/353,426

(22) Filed: Jan. 19, 2012

(65) Prior Publication Data

US 2012/0190084 A1    Jul. 26, 2012

(30) Foreign Application Priority Data

Jan. 20, 2011 (EP) .................................... 11151526

(51) Int. Cl.
| | | |
|---|---|---|
| *C07H 21/04* | (2006.01) | |
| *C12P 13/12* | (2006.01) | |
| *C12N 1/21* | (2006.01) | |
| *C12N 9/10* | (2006.01) | |
| *C12R 1/15* | (2006.01) | |

(52) U.S. Cl.
CPC . *C12P 13/12* (2013.01); *C12N 9/13* (2013.01); *C12Y 208/01001* (2013.01); *C12R 1/15* (2013.01)

(58) Field of Classification Search
None
See application file for complete search history.

(56) References Cited

U.S. PATENT DOCUMENTS

| 6,815,196 B2 | 11/2004 | Bathe et al. |
| 6,942,996 B2 | 9/2005 | Bathe et al. |
| 6,958,228 B2 | 10/2005 | Bathe et al. |

FOREIGN PATENT DOCUMENTS

| EP | 1528108 A1 | 5/2005 |
| WO | 01/27307 A1 | 4/2001 |
| WO | 2007/011939 A2 | 1/2007 |
| WO | 2007/077041 A1 | 7/2007 |
| WO | 2007/135188 A2 | 11/2007 |
| WO | 2009/043803 A2 | 4/2009 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Accession Q08742. Nov. 1, 1996.*
International Search Report received in PCT/EP2012/050417, mailed Apr. 10, 2012.
European Search Report received in EP11151526, mailed Nov. 4, 2011.
Krömer, J.O. et al. (2006) "Metabolic Pathway Analysis for Rational Design of L-methionine Production by *Escherichia coli* and *Corynebacterium glutamicum*" Metabolic Engineering, 8:353-369.
Kessler, D. (2006) "Enzymatic Activation of Sulfur for Incorporation into Biomolecules in Prokaryotes" FEMS Microbiology Reviews, 30:825-840.
Nardiz, N. et al. (2010) "A Rhondanese-like Protein is Highly Over-represented in the Mutant *S. Clavuligerus* oppA2::aph: Effect on Holomycin and Other Secondary Metabolites Production" Microbial Biotechnology, 4(2):216-225.
Cheng, Hui, et al. (2008) "Biochemical and Genetic Characterization of PspE and GIpE, Two Single-Domain Sulfurtransferases of *Escherichia coli*" The Open Microbiology Journal, 2:18-28.
Foster, M.W., et al. (2009) "A Protein Microarray-based Analysis of S-nitrosylation" Proceedings of the National Academy of Sciences, 106(45):18948-18953.

* cited by examiner

*Primary Examiner* — Christian Fronda
(74) *Attorney, Agent, or Firm* — Smith, Gambrell & Russell, LLP

(57) ABSTRACT

Disclosed herein is a process for the fermentative preparation of sulphur-containing amino acids chosen from the group of L-methionine, L-cysteine, L-cystine, L-homocysteine and L-homocystine, comprising the steps: a) provision of a microorganism of the family Enterobacteriaceae or of a microorganism of the family Corynebacteriaceae which has an increased thiosulphate sulphurtransferase activity compared with the particular starting strain; b) fermentation of the microorganism from a) in a medium which contains an inorganic source of sulphur chosen from the group of salt of dithiosulphuric acid or a mixture of a salt of dithiosulphuric acid and a salt of sulphuric acid, a fermentation broth being obtained, and c) concentration of the sulphur-containing amino acid in the fermentation broth from b).

2 Claims, 1 Drawing Sheet

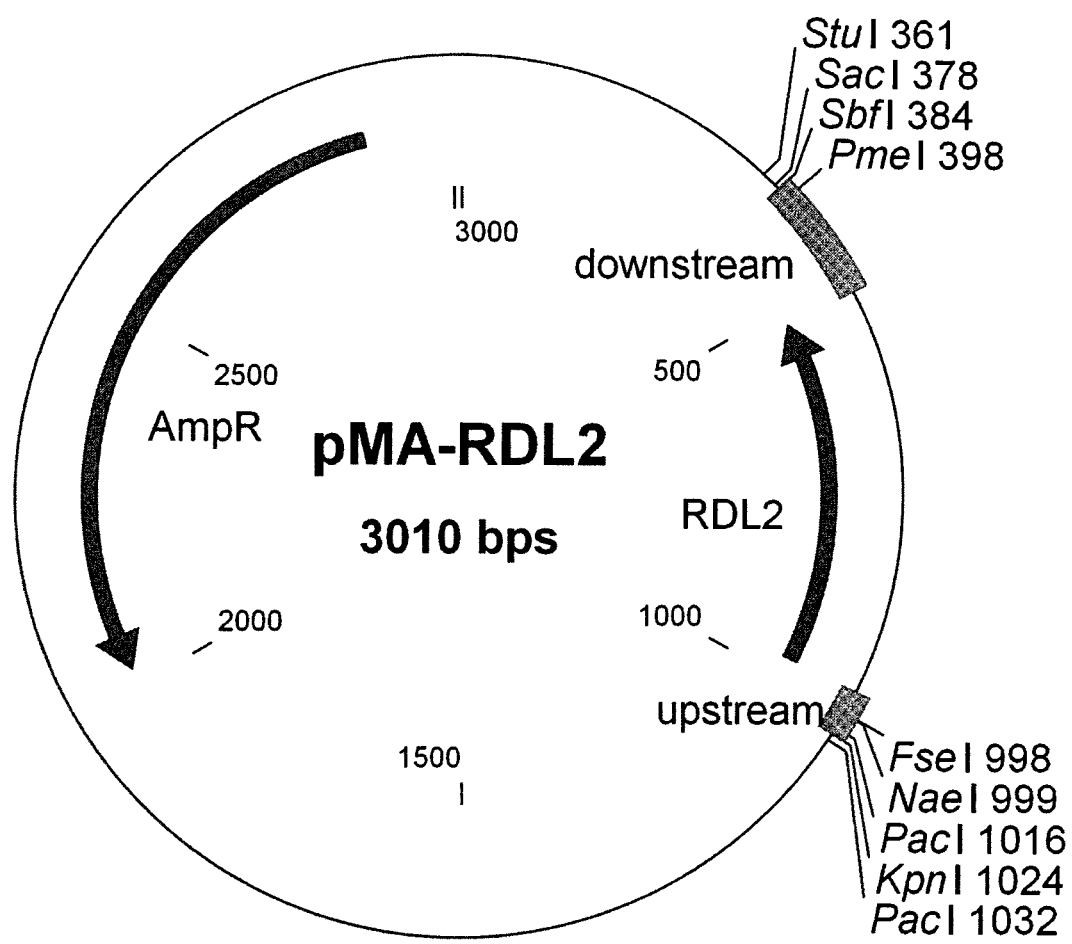

PROCESS FOR THE FERMENTATIVE PREPARATION OF SULPHUR-CONTAINING AMINO ACIDS

The invention relates to a process for the fermentative preparation of sulphur-containing amino acids chosen from the group of L-methionine, L-cysteine, L-cystine, L-homocysteine and L-homocystine.

Sulphur-containing amino acids are of great economic importance. L-Cysteine is used as a food additive, as a starting substance for pharmacological active compounds (e.g. N-acetylcysteine) and for cosmetics. The amino acid L-methionine plays a prominent role in animal nutrition. It belongs to the essential amino acids which cannot be produced by biosynthesis in the metabolism of vertebrates. In animal breeding it must consequently be ensured that adequate amounts of methionine are taken in with the feed. However, since L-methionine is often present in conventional feedstuff plants (such as soya or cereals) in amounts which are too low to ensure optimum animal nutrition, especially for pigs and poultry, it is advantageous to admix methionine as an additive to the animal feed. D-Methionine can be converted into biologically active L-methionine by vertebrates. A racemate of D- and L-methionine is therefore usually added to the animal feed. L-Homocysteine can be converted into L-methionine by animals by transmethylation and can therefore replace this.

In the prior art, amino acids such as methionine are prepared by chemical synthesis. In this preparation, acrolein and methylmercaptan are first reacted to give 3-methylthiopropionaldehyde, which in turn with cyanide, ammonia and carbon monoxide leads to hydantoin. This can finally be hydrolysed to the racemate, an equimolar mixture of the two stereoisomers D- and L-methionine. Since the biologically active form of the molecule represents exclusively the L form, the D form contained in the feed must first be converted into the active L form in the metabolism by de- and transamination.

In contrast to methionine, most other natural, proteinogenic amino acids are chiefly prepared by fermentation by microorganisms. This utilizes the fact that microorganisms have appropriate biosynthesis pathways for synthesis of the natural amino acids. In addition, many fermentation processes achieve very favourable production costs with inexpensive educts, such as glucose and mineral salts, and moreover deliver the biologically active L form of the particular amino acid.

However, biosynthesis pathways of amino acids are subject to strict metabolic control in wild-type strains, which ensures that the amino acids are produced only for the cell's own requirement. An important prerequisite for efficient production processes is therefore that suitable microorganisms are available which, in contrast to the wild-type organisms, have a drastically increased production output for the preparation of the desired amino acid.

Such microorganisms which overproduce amino acids can be produced by conventional mutation/selection processes and/or by modern, targeted, recombinant techniques (metabolic engineering). In the latter case, genes or alleles which effect an amino acid overproduction by their modification, activation or inactivation are first identified. These genes/alleles are then introduced into a microorganism strain or inactivated by molecular biology techniques, so that an optimum overproduction is achieved. However, often only the combination of several different measures leads to a truly efficient production.

In *E. coli* and *C. glutamicum*, L-cysteine is derived biochemically from L-serine. L-Serine is activated as O-acetylserine by the serine acetyltransferase CysE. The O-acetylserine (thiol)lyase then transfers reduced sulphur in the form of sulphide, as a result of which L-cysteine is formed. In contrast to *C. glutamicum*, *E. coli* has two different O-acetylserine (thiol)lyases, the O-acetylserine (thiol)lyase B ("CysM") also being able to transfer thiosulphate to O-acetylserine. As a result, S-sulphocysteine is formed, which is then split into L-cysteine and sulphite or sulphate in a manner which has not yet been characterized (Kredich N. M. (1996) in Neidhardt F C et al. (ed.) "*Escherichia coli* and *Salmonella*", 2nd edition, p. 514-527).

L-Methionine, together with lysine and threonine, is derived from aspartate. Sulphur is introduced in the form of L-cysteine (via cystathionine as an intermediate product) into L-methionine by transsulphurization (in *C. glutamicum* and *E. coli*; only route in *E. coli*). In parallel with this, e.g. in *C. glutamicum* there is the route of direct sulfhydrylation, in which sulphide is assimilated in the form of L-homocysteine (B-J Hwang, H-J Yeom, Y Kim, H-S Lee, 2002, J. Bacteriol., 184(5): 1277-1286). The C1 group of the L-methionine originates from the C1 metabolism and it is transferred to L-homocysteine by the methionine synthases MetE and MetH (Review: Greene R C (1996) in Neidhardt F C et al. (ed.) "*Escherichia coli* and *Salmonella*", 2nd edition, p. 542-560). L-Methionine biosynthesis in *C. glutamicum* is described by Rückert et al. (Rückert C, Pühler A, Kalinowski J, 2003, J Biotechnol., 104(1-3):213-28). Strains and processes for the fermentative production of L-methionine have been described e.g. for *E. coli* (WO2006/001616, WO2009/043803) and *C. glutamicum* (WO2009/144270).

The use of thiosulphate as a source of sulphur allows significantly higher theoretical yields in the production of sulphur-containing amino acids (compared with sulphate) (Krömer J O, Wittmann C, Schröder H, Heinzle E, Metab Eng., 2006, 8 (4), pp. 353-369; and WO2007/020295). The advantage of thiosulphate is explained as follows: In sulphate ($SO_4^{2-}$) the sulphur atom is present in oxidation level +6. For assimilation, it must be reduced to oxidation level −2 (sulphide=$S^{2-}$). For reduction of a sulphate to sulphide, the cell must use 2 ATP and 4 NADPH (=8 electrons). In thiosulphate, the central sulphur atom has the oxidation level +5, and the terminal sulphur atom has the oxidation level −1 (average formal oxidation level of the two sulphur atoms: +2). For reduction of both the sulphur atoms of thiosulphate, only 8 electrons are therefore required, compared with 16 electrons in the reduction of 2 sulphates.

The use of thiosulphate as a source of S for the production of L-cysteine with *E. coli* is described e.g. in DE 10 2007 007 333 and WO2001/27307.

It has been shown in WO2007/077041 that L-methionine production in *E. coli* can also be improved significantly by the use of thiosulphate instead of sulphate.

It has not yet hitherto been shown experimentally that the use of thiosulphate also leads to an improvement in L-methionine production in *C. glutamicum*. It is shown in WO2007/020295 (p. 240) that with Na thiosulphate as a source of sulphur, *C. glutamicum* forms more biomass. This was evaluated as an indication of the lower ATP and NADPH consumption. L-Methionine production with thiosulphate was not investigated in practice.

In *E. coli*, thiosulphate is taken up by the sulphate/thiosulphate transporter CysPUWA-Sbp (Kredich N. M. (1996) in Neidhardt F C et al. (ed.) "*Escherichia coli* and *Salmonella*", 2nd edition, p. 514-527). CysP and Sbp are two different periplasmic binding proteins. CysP has a higher affinity for thiosulphate and Sbp has a higher affinity for sulphate. CysA forms the ATP-binding component. CysU and CysW are the transmembrane components. In WO2009/043803, the expression of the cysPUWAM operon was amplified in *E. coli* and an improvement in L-methionine production was thereby achieved. Nothing is known of the uptake of thiosulphate in *C. glutamicum*. Knock out mutants of the putative sulphate uptake system CysZ (cg3112) can still grow with thiosulphate as the source of S (Ruckert C. et al. (2005), BMC Genomics., vol. 6(121)). CysZ is therefore not (solely) responsible for transport of thiosulphate.

O-Acetylserine (thiol)lyase B (=CysM, EC 2.5.1.47) makes it possible for *E. coli* to use thiosulphate as a source of S for the synthesis of L-cysteine and L-methionine. The enzyme catalyses the formation of S-sulphocysteine (R—S—$SO_3$) and acetate from O-acetylserine and thiosulphate. S-Sulphocysteine is then cleaved into L-cysteine and sulphite or sulphate in a manner which has not hitherto been characterized (Kredich N. M. (1996) in Neidhardt F C et al. (ed.) "*Escherichia coli* and *Salmonella*", 2nd edition, p. 514-527). The sulphate is reduced to sulphite ($SO_3^{2-}$) in three steps by ATP sulphurylase (CysDN), APS kinase (CysC) and PAPS sulphotransferase (CysH). Sulphite is then reduced further by NADPH sulphite reductase to give sulphide ($S^2$), which can be used by O-acetylserine (thiol)lyase A (CysK) and O-acetylserine (thiol)lyase B (CysM) for synthesis of a second L-cysteine molecule.

*C. glutamicum* can grow in minimal medium with thiosulphate as a source of sulphur (Ruckert C. et al. (2005), BMC Genomics., vol. 6(121)). Nevertheless, *C. glutamicum* has no O-acetylserine (thiol)lyase B ("CysM") (Ruckert and Kalinowski (2008) in A. Burkovski (ed.) "*Corynebacteria*: Genomics and Molecular Biology", Caister Academic Press). Thiosulphate must therefore be assimilated in another manner.

The object of the present invention is to provide a process and microorganism strains which render possible a higher overproduction of sulphur-containing amino acids, in particular of L-methionine.

This object is achieved by a process for the fermentative preparation of sulphur-containing amino acids chosen from the group of L-methionine, L-cysteine, L-cystine, L-homocysteine and L-homocystine, comprising the steps:
  a) provision of a microorganism of the family Enterobacteriaceae or of a microorganism of the family Corynebacteriaceae which has an increased thiosulphate sulphurtransferase activity compared with the particular starting strain;
  b) fermentation of the microorganism from a) in a medium which contains a salt of dithiosulphuric acid or a mixture of a salt of dithiosulphuric acid and a salt of sulphuric acid as an inorganic source of sulphur, a fermentation broth being obtained, and
  c) concentration of the sulphur-containing amino acid in the fermentation broth from b).

The invention furthermore provides a process for the fermentative preparation of sulphur-containing amino acids chosen from the group of L-methionine, L-cysteine, L-cystine, L-homocysteine and L-homocystine, comprising the steps:
  a) provision of a microorganism of the family Enterobacteriaceae or of a microorganism of the family Corynebacteriaceae which overexpresses a gene coding for a polypeptide with the activity of a thiosulphate sulphurtransferase;
  b) fermentation of the microorganism from a) in a medium which contains a salt of dithiosulphuric acid or mixture of a salt of dithiosulphuric acid and a salt of sulphuric acid as an inorganic source of sulphur, a fermentation broth being obtained, and
  c) concentration of the sulphur-containing amino acid in the fermentation broth from b).

Thiosulphate sulphurtransferases, also called "rhodaneses" (EC 2.8.1.1), are enzymes which transfer the reduced sulphur atom from thiosulphate to cyanide ($CN^-$).

Some thiosulphate sulphurtransferases can also transfer the reduced sulphur atom to alternative substrates, e.g. dihydrolipoate (Alexander K., Volini M, 1987, J. Biol. Chem., 262: 6595-6604). In the database "Clusters of Orthologous Groups of proteins" (COG), 168 homologous sulphurtransferases in all three domains of life are currently to be found in category COG0607 "Rhodanese-related sulphurtransferase" (Tatusov R L, Fedorova N D, Jackson J D, Jacobs A R, Kiryutin B, Koonin E V, Krylov D M, Mazumder R, Mekhedov S L, Nikolskaya A N, Rao B S, Smirnov S, Sverdlov A V, Vasudevan S, Wolf Y I, Yin J J, Natale D A, 2003, BMC Bioinformatics, 4:41; http//www.ncbi.nlm.nih.gov/COG/). Rhodaneses have one or more characteristic rhodanese-like domains (PFAM database PF00581, http://pfam.sanger.ac.uk/; Gliubich F, Gazerro M, Zanotti G, Delbono S, Bombieri G, Berni R, 1996, J Biol. Chem., 271(35):21054-61).

The gene RDL2 (rhodanese-like protein) from *Saccharomyces cerevisiae* S288c codes for the protein Rdl2p 149 amino acids long. It has a rhodanese-like domain (PFAM database PF00581, http//pfam.sanger.ac.uk/). It has been shown by experiment that Rdl2p is a thiosulphate sulphurtransferase (rhodanese, EC 2.8.1.1; Foster M W, Forrester M T, Stamler J S, 2009, Proc Natl Acad Sci USA, 106(45):18948-53). SEQ ID NO: 1 shows the DNA sequence of the gene RDL2. SEQ ID NO: 2 shows the amino acid sequence of the protein Rdl2p coded by RDL2.

*E. coli* has, in addition to the well-characterized rhodaneses GlpE and PspE (Adams H, Teertstra W, Koster M, Tommassen J, 2002, FEBS Lett. 518:173-6), seven further paralogous enzymes with rhodanese-like domains (Cheng H, Donahue J L, Battle S E, Ray W K, Larson T J, 2008, Open Microbiol J., 2:18-28):

YgaP has an N-terminal rhodanese-like domain and two transmembrane domains. It shows in vitro rhodanese activity (Ahmed, F., 2003, Dissertation).

YbbB is a tRNA 2-selenouridine synthase and has an N-terminal rhodanese-like domain (Wolfe M D, Ahmed F, Lacourciere G M, Lauhon C T, Stadtman T C, Larson T J, 2004, J Biol. Chem., 279(3):1801-1809).

ThiI is necessary for synthesis of thiamine and plays a role in the conversion of uridine into thiouridine at position 8 in tRNA (Palenchar P M, Buck C J, Cheng H, Larson T J, Mueller E G, 2000, J Biol. Chem., 275(12):8283-8286).

SseA is a 3-mercaptopyruvate:cyanide sulphurtransferase, which preferentially transfers 3-mercaptopyruvate instead of thiosulphate to cyanide (Colnaghi R, Cassinelli G, Drummond M, Forlani F, Pagani S, 2001, FEBS Lett., 500(3):153-156). The enzyme has two rhodanese-like domains.

The ORF ynjE codes for a putative sulphurtransferase with three rhodanese-like domains (Hanzelmann P, Dahl J U, Kuper J, Urban A, Müller-Theissen U, Leimkühler S, Schindelin H., 2009, Protein Sci., 18(12):2480-2491).

The ORF yibN codes for a putative sulphurtransferase with a C-terminal rhodanese-like domain.

The ORF yceA codes for a putative sulphurtransferase with a rhodanese-like domain.

In *Corynebacterium glutamicum*, at least 7 ORFs code for presumed sulphurtransferases:

The ORF thtR (=cg0803, NCgl0671) codes for a putative sulphurtransferase with two rhodanese-like domains and a length of 301 amino acids.

The ORF sseA2 (=cg1613, NCgl1369) codes for a putative sulphurtransferase with two rhodanese-like domains and a length of 289 amino acids.

The ORF cg3000 (=NCgl2616) codes for a putative sulphurtransferase with a rhodanese-like domain and a length of 96 amino acids.

The ORF cg0073 (=NCgl0053) codes for a putative sulphurtransferase with a rhodanese-like domain and a length of 97 amino acids.

The ORF cg0074 (=NCgl0054) codes for a putative sulphurtransferase with a rhodanese-like domain and a length of 197 amino acids.

The ORF sseA1 (=cg3073, NCgl2678) codes for a putative sulphurtransferase with two rhodanese-like domains and a length of 274 amino acids.

The ORF cg3319 (=NCgl2890) codes for a putative sulphurtransferase with a rhodanese-like domain and a length of 312 amino acids.

The thiosulphate sulphurtransferase from cattle (Bos taurus) has two rhodanese-like domains and is well-characterized (Cannella C, Costa M, Pensa B, Ricci G, Pecci L, Cavallini D., 1981, Eur J. Biochem., 119(3):491-495).

In a preferred embodiment of the process, the microorganism overexpresses one or more gene(s) coding for a polypeptide with the activity of a thiosulphate sulphurtransferase, the polypeptide with the activity of a thiosulphate sulphurtransferase being chosen from the following a) to d):

a) a polypeptide consisting of or containing the polypeptides Rdl2p, GlpE, PspE, YgaP, ThiI, YbbB, SseA, YnjE, YceA, YibN, NClg0671, NCgl1369, NCgl2616, NCgl0053, NCgl0054, NCgl2678, NCgl2890; thiosulphate sulphurtransferase from mammals, for example the thiosulphate sulphurtransferase from the bovine liver (Bos taurus); preferably Rdl2p, GlpE, PspE and particularly preferably Rdl2p;

b) a polypeptide consisting of or containing the amino acid sequence shown in SEQ ID NO: 2;

c) a polypeptide with an amino acid sequence which is identical to the extent of 70% or more to the amino acid sequence of a) or b), the polypeptide having thiosulphate sulphurtransferase activity;

d) a polypeptide which has an amino acid sequence containing a deletion, substitution, insertion and/or addition of from 1 to 45 amino acid residues with respect to the amino acid sequence shown in SEQ ID NO: 2, the polypeptide having thiosulphate sulphurtransferase activity.

As mentioned above, polypeptides with the activity of a thiosulphate sulphurtransferase also include variants of the enzymes mentioned under a) or b), with an amino acid sequence which is identical to the extent of 70% or more to the amino acid sequence of the sequences mentioned under a) or b), the variants having thiosulphate sulphurtransferase activity. Preferred embodiments include variants which are at least 75%, at least 80%, at least 85%, at least 90%, at least 95%, at least 98% or at least 99% identical to the amino acid sequences described above, i.e. wherein at least 75%, at least 80%, at least 85%, at least 90%, at least 95%, at least 98% or at least 99% of the amino acid positions are identical to those of the amino acid sequences described above. The percentage identity is preferably calculated over the total length of the amino acid or nucleic acid region. A number of programs based on a large number of algorithms are available to the person skilled in the art for sequence comparison. In this connection, the algorithms of Needleman and Wunsch or Smith and Waterman give particularly reliable results. For the alignment of the sequences, the program PileUp (J. Mol. Evolution., 25, 351-360, 1987, Higgins et al., CABIOS, 5 1989: 151-153) or the programs Gap and BestFit [Needleman and Wunsch (J. Mol. Biol. 48; 443-453 (1970)) and Smith and Waterman (Adv. Appl. Math. 2; 482-489 (1981))], which belong to the GCG software package [Genetics Computer Group, 575 Science Drive, Madison, Wis., USA 53711 (1991)] are available. The percentage values given above for the sequence identity are preferably calculated over the total sequence region with the GAP program.

Polypeptides with the activity of a thiosulphate sulphurtransferase furthermore also include fragments of the enzymes mentioned in a) or b). These fragments have the activity described above. A fragment of a polypeptide with the activity of a thiosulphate sulphurtransferase in the context of this patent application preferably contains at least 30, at least 50, or at least 80 successive amino acid residues of one of the abovementioned amino acid sequences. As mentioned above, polypeptides with the activity of a thiosulphate sulphurtransferase also include variants of the enzymes mentioned under a) or b) which have an amino acid sequence containing a deletion, substitution, insertion and/or addition of from 1 to 45 amino acid residues with respect to the amino acid sequence shown in SEQ ID NO: 2, the polypeptide having thiosulphate sulphurtransferase activity. In preferred embodiments, the amino acid sequence contains a deletion, substitution, insertion and/or addition of from 1 to 40, further preferably from 1 to 30, still further preferably from 1 to 20, preferably from 1 to 15, still further preferably from 1 to 10 and most preferably from 1 to 5 amino acid residues with respect to the amino acid sequence shown in SEQ ID NO: 2.

In a further preferred process, the polypeptide is coded by a gene which includes the nucleotide sequence of SEQ ID NO: 1, which corresponds to the wild-type sequence of the gene RDL2 from Saccharomyces cerevisiae S288c.

It is furthermore preferable for the polypeptide to be coded by a gene which includes the nucleotide sequence of SEQ ID NO: 3. The codon usage here is slightly adapted to that of E. coli.

In a further preferred process, the polypeptide is coded by a gene which includes the nucleotide sequence of SEQ ID NO: 4. The codon usage here is more highly adapted to that of E. coli.

It is furthermore preferable for the polypeptide to be coded by a gene which includes the nucleotide sequence of SEQ ID NO: 5. The codon usage here is adapted completely to that of E. coli.

In carrying out the process according to the invention, the expression of the gene coding for a polypeptide with the activity of a thiosulphate sulphurtransferase is preferably increased by one or more of the following measures:

a) The expression of the gene is under the control of a promoter which, in the microorganism used for the process, leads to an amplified expression compared with the starting strain. In this context, for example, a constitutive GAPDH promoter of the gapA gene of Escherichia coli, or an inducible lac, tac, trc, lambda, ara or tet promoter can be used (Review: Makrides S C. Micro-biol Rev. 1996 September; 60(3):512-38).

b) The number of copies of the gene coding for a polypeptide with the activity of a thiosulphate sulphurtransferase is increased compared with the starting strain. This can be achieved, for example, by inserting the gene into plasmids with an increased number of copies, or by integrating the gene into the chromosome of the microorganism in several copies (Baneyx F, 1999, Curr. Opin. Biotechnol. 10, 411-421).

c) The expression of the gene is effected using a ribosome binding site, which leads to an increased translation in the microorganism used for the process compared with the starting strain (Makrides S C. Microbiol. Rev. 1996 September; 60(3):512-38).
d) The expression of the gene is amplified by optimization of the codon usage of the gene with respect to the microorganism used for the process (Welch, Villalobos, Gustafsson and Minshull, J R Soc Interface, 2009, 6:S467-76). The codon adaptation index (CAI), for example, is suitable as a measure of the adaptation of the codon usage of a gene to an organism (Sharp P M, Li W H, 1987, Nucleic Acids Res., 15(3):1281-95).
e) The expression of the gene is amplified by reduction of mRNA secondary structures in the mRNA transcribed by the gene (Kudla G, Murray A W, Tollervey D, Plotkin J B., Science, 2009 Apr. 10; 324(5924):255-8; Welch, Villalobos, Gustafsson and Minshull, J R Soc Interface, 2009, 6:S467-76).
f) The expression of the gene is amplified by elimination of RNA polymerase terminators in the mRNA transcribed by the gene (Welch, Villalobos, Gustafsson and Minshull, J R Soc Interface, 2009, 6:S467-76).
g) The expression of the gene is effected using mRNA-stabilizing sequences in the mRNA transcribed by the gene (Carrier T A, Keasling J D, Biotechnol Prog., 1997, November-December; 13(6):699-708). The sequence ARNmst17 may be mentioned as an example for stabilizing the mRNA of the gene metF of *E. coli* (WO2009/043803).

In a further embodiment of the process according to the invention, it is preferable for the salt of dithiosulphuric acid to be a salt chosen from the group of alkali metal salt, alkaline earth metal salt, ammonium salt and mixtures thereof, preferably ammonium salt.

It is furthermore preferable for the salt of sulphuric acid to be a salt chosen from the group of alkali metal salt, alkaline earth metal salt, ammonium salt (and mixtures), preferably ammonium salt.

Preferably, the concentration of the salt of dithiosulphuric acid in the medium or in the fermentation broth is 0.05 g/kg to 100 g/kg, preferably 0.1 g/kg to 20 g/kg and particularly preferably 0.2 g/kg to 12 g/kg.

In a preferred process, the concentration of the salt of dithiosulphuric acid in the medium or in the fermentation broth during the fermentation is kept at least 0.05 g/kg to 100 g/kg, preferably 0.1 g/kg to 20 g/kg and particularly preferably 0.2 g/kg to 12 g/kg.

In a further preferred process, during the fermentation the content of the salt of dithiosulphuric acid, based on the total content of inorganic sulphur in the medium and in the fermentation broth, is kept at least 5 mol %.

The process according to the invention can be designed as a batch process, fed batch process, repeated fed batch process and continuous process.

The sulphur-containing amino acid can furthermore be obtained from the fermentation broth as a solid product or in dissolved form in a liquid product.

In a preferred process of the present invention, the sulphur-containing amino acid to be produced is L-methionine.

It is furthermore preferable for the microorganism to be the genus *Escherichia*, particularly preferably the species *Escherichia coli*.

In an alternative process, the microorganism is the genus *Corynebacterium*, particularly preferably the species *Corynebacterium glutamicum*.

In a particularly preferred process of the present invention, the microorganism is chosen from:
*Corynebacterium glutamicum* with increased activity and/or expression of aspartate kinase and attenuation or deletion of the regulator protein McbR compared with the starting strain;
*Escherichia coli* with increased activity and/or expression of aspartate kinase and attenuation or deletion of the regulator protein MetJ compared with the starting strain.

The invention furthermore provides a microorganism chosen from
*Corynebacterium glutamicum* with increased activity and/or expression of aspartate kinase and attenuation or deletion of the regulator protein McbR compared with the starting strain;
*Escherichia coli* with increased activity and/or expression of aspartate kinase and attenuation or deletion of the regulator protein MetJ compared with the starting strain;
wherein the microorganism secretes or produces L-methionine, and wherein the microorganism has an increased thiosulphate sulphurtransferase activity compared with the particular starting strain.

The invention moreover provides a microorganism chosen from
*Corynebacterium glutamicum* with increased activity and/or expression of aspartate kinase and attenuation or deletion of the regulator protein McbR compared with the starting strain;
*Escherichia coli* with increased activity and/or expression of aspartate kinase and attenuation or deletion of the regulator protein MetJ compared with the starting strain;
wherein the microorganism secretes or produces L-methionine, and wherein the microorganism overexpresses a gene coding for a polypeptide with the activity of a thiosulphate sulphurtransferase.

The strain of *C. glutamicum* which secretes or produces L-methionine preferably has an increased enzyme activity of aspartate kinase (EC 2.7.2.4), feedback-resistant alleles being preferred. In the *Corynebacterium*, this aspartate kinase is coded by the gene lysC. Due to the attenuation or deletion of the regulator protein McbR (which is coded by the gene mcbR), an increase in the sulphur utilization furthermore takes place. McbR is the repressor of the entire sulphur utilization cascade in *C. glutamicum* (Rey D A, Nentwich S S, Koch D J, Ruckert C, Puhler A, Tauch A, Kalinowski J., Mol. Microbiol., 2005, 56(4):871-887).

The strain of *E. coli* which secretes or produces L-methionine preferably has an increased enzyme activity of aspartate kinase (EC 2.7.2.4), feedback-resistant alleles being preferred. In *E. coli* there are three different aspartate kinases which are coded by the genes thrA, metL or lysC. Due to the attenuation or deletion of the regulator protein MetJ, which is coded by the gene metJ, an increase in the L-methionine biosynthesis furthermore takes place. MetJ is the main repressor of L-methionine biosynthesis in *E. coli*.

It is furthermore preferable for this microorganism to overexpress one or more gene(s) coding for a polypeptide with the activity of a thiosulphate sulphurtransferase, the polypeptide with the activity of a thiosulphate sulphurtransferase being chosen from the following a) to d):
a) a polypeptide consisting of or containing the polypeptides Rdl2p, GlpE, PspE, YgaP, ThiI, YbbB, SseA, YnjE, YceA, YibN, NCgl0671, NCgl1369, NCgl2616, NCgl0053, NCgl0054, NCgl2678, NCgl2890; thiosulphate sulphurtransferase from mammals, for example the thiosulphate sulphurtransferase from the bovine liver (*Bos taurus*); preferably Rdl2p, GlpE, PspE and particularly preferably Rdl2p;

b) a polypeptide consisting of or containing the amino acid sequence shown in SEQ ID NO: 2;

c) a polypeptide with an amino acid sequence which is identical to the extent of 70% or more to the amino acid sequence of a) or b), the polypeptide having thiosulphate sulphurtransferase activity;

d) a polypeptide which has an amino acid sequence containing a deletion, substitution, insertion and/or addition of from 1 to 45 amino acid residues with respect to the amino acid sequence shown in SEQ ID NO: 2, the polypeptide having thiosulphate sulphurtransferase activity.

The starting strain of the microorganism furthermore is preferably derived from the group consisting of *Escherichia coli* MG1655, *Escherichia coli* W3110, *Escherichia coli* DH5α, *Escherichia coli* DH10B, *Escherichia coli* BW2952, *Escherichia coli* REL606, *Corynebacterium glutamicum* ATCC13032, *Corynebacterium glutamicum* R, *Corynebacterium glutamicum* DSM20411 (former name *Brevibacterium flavum*), *Corynebacterium glutamicum* DSM20412 (former name *Brevibacterium lactofermentum*), *Corynebacterium glutamicum* DSM1412 (former name *Brevibacterium lactofermentum*), *Corynebacterium efficiens* YS-314$^T$ (=DSM44549), *Corynebacterium glutamicum* ATCC21608, *Corynebacterium glutamicum* DSM17322.

A further strain which secretes or produces L-methionine is, for example, the *E. coli* production strain MG1655 ΔmetJ Ptrc-metH Ptrc-metF PtrcF-cysPUWAM Ptrc-cysJIH Ptrc09-gcvTHP containing the production plasmid pME101-thrA*1-cysE-Pgap-metA*11 (WO2009/043803).

Cloning of the *E. coli* production strain MG1655ΔmetJ Ptrc-metH Ptrc-metF PtrcF-cysPUWAM Ptrc-cysJIH Ptrc09-gcvTHP is described in the patent application WO2009/043803. The strain is based on the wild-type strain *E. coli* K12 MG1655. The following modifications have been introduced in the genome of this strain:

The gene for the repressor to L-methionine biosynthesis metJ has been deleted.

Upstream of the gene metH (codes for cobalamin-dependent methionine synthase), the potent trc promoter has been inserted.

Upstream of the gene metF (codes for 5,10-methylenetetrahydrofolate reductase), the potent trc promoter has been inserted.

Upstream of the operon cysPUWAM, the potent trcF promoter has been inserted. cysPUWA codes for a sulphate/thiosulphate uptake transporter. cysM codes for cysteine synthase B.

Upstream of the operon cysJIH, the potent trcF promoter has been inserted. cysJI codes for sulphite reductase and cysH codes for 3'-phosphoadenylyl sulphate reductase.

Upstream of the operon gcvTHP, the potent trc09 promoter has been inserted. gcvT, gcvH and gcvP code for three components of the glycine cleavage system.

Cloning of the *E. coli* production plasmid pME101-thrA*1-cysE-Pgap-metA*11 is described in the patent application WO2007/077041. It is a plasmid with a low number of copies (low copy plasmid) based on the vector pCL1920 (Lerner, C. G. and Inouye, M., Nucl. Acids Res. (1990) 18:4631[PMID: 2201955]). The empty plasmid pME101 has the lacI$^q$ gene, which codes for a highly expressed allele of the lac repressor. The gene thrA*1 was cloned downstream of a potent trc promoter which can be repressed by the Lac repressor. It codes for a feedback-resistant variant of aspartate kinase/homoserine dehydrogenase ThrA from *E. coli*. In the same orientation after it lies the gene cysE together with its natural promoter. It codes for serine acetyltransferase from *E. coli*. Downstream of cysE, the potent gapA promoter from *E. coli* follows, which controls the expression of the gene metA*11. metA*11 codes for a feedback-resistant variant of homoserine O-succinyltransferase from *E. coli*.

The following strains may be mentioned as examples of further microorganisms which secrete or produce L-methionine:

*C. glutamicum* M1179 (=DSM17322) (WO2007/011939)

*E. coli* TF4076BJF metA#10+metYX(Lm) (WO2008/127240; page 46);

*E. coli* W3110ΔJ/pKP451 (EP 1 445 310 B1, page 7 ex. 4)

*E. coli* WΔthrBCΔmetJmetK32 pMWPthrmetA4Δ5Δ9 (Yoshihiro Usuda and Osamu Kurahashi, 2005, Applied and Environmental Microbiology, vol. 71, no. 6, p. 3228-3234)

W3110/pHC34 (WO01/27307 page 13, ex. 3).

Further examples of various suitable microorganisms are described by Gomes et al. (Enzyme and Microbial Technology (2005), 3-18).

In further preferred embodiments, the bacteria which produce L-methionine have one or more features chosen from the group of:

1) overexpressed polynucleotide which codes for one or more components of the thiosulphate/sulphate transport system CysPUWA (EC 3.6.3.25),
2) overexpressed polynucleotide which codes for a 3'-phosphoadenosine 5'-phosphosulphate reductase CysH (EC 1.8.4.8),
3) overexpressed polynucleotide which codes for one or more components of the sulphite reductase CysJI (EC 1.8.1.2),
4) overexpressed polynucleotide which codes for a cysteine synthase A CysK (EC 2.5.1.47),
5) overexpressed polynucleotide which codes for a cysteine synthase B CysM (EC 2.5.1.47),
6) overexpressed polynucleotide which codes for a serine acetyltransferase CysE (EC 2.3.1.30),
7) overexpressed polynucleotide which codes for one or more components of the glycine cleavage system GcvTHP-Lpd (EC 2.1.2.10, EC 1.4.4.2, EC 1.8.1.4),
8) overexpressed polynucleotide which codes for a lipoyl synthase LipA (EC 2.8.1.8),
9) overexpressed polynucleotide which codes for a lipoyl protein ligase LipB (EC 2.3.1.181),
10) overexpressed polynucleotide which codes for a phosphoglycerate dehydrogenase SerA (EC 1.1.1.95),
11) overexpressed polynucleotide which codes for a 3-phosphoserine phosphatase SerB (EC 3.1.3.3),
12) overexpressed polynucleotide which codes for a 3-phosphoserine/phosphohydroxythreonine aminotransferase SerC (EC 2.6.1.52),
13) overexpressed polynucleotide which codes for a serine hydroxymethyltransferase GlyA (EC 2.1.2.1),
14) overexpressed polynucleotide which codes for an aspartokinase I and homoserine dehydrogenase I ThrA (EC 2.7.2.4, EC 1.1.1.3),
15) overexpressed polynucleotide which codes for an aspartate kinase LysC (EC 2.7.2.4),
16) overexpressed polynucleotide which codes for a homoserine dehydrogenase Hom (EC 1.1.1.3),
17) overexpressed polynucleotide which codes for a homoserine O-acetyltransferase MetX (EC 2.3.1.31),
18) overexpressed polynucleotide which codes for a homoserine O-succinyltransferase MetA (EC 2.3.1.46), 19) overexpressed polynucleotide which codes for a cystathionine gamma-synthase MetB (EC 2.5.1.48),
20) overexpressed polynucleotide which codes for a β-C—S-lyase AecD (EC 4.4.1.8, also called beta-lyase),
21) overexpressed polynucleotide which codes for a cystathionine beta-lyase MetC (EC 4.4.1.8),
22) overexpressed polynucleotide which codes for a B12-independent homocysteine S-methyltransferase MetE (EC 2.1.1.14),
23) overexpressed polynucleotide which codes for a B12-dependent homocysteine S-methyltransferase MetH (EC 2.1.1.13),
24) overexpressed polynucleotide which codes for a methylenetetrahydrofolate reductase MetF (EC 1.5.1.20),
25) overexpressed polynucleotide which codes for one or more components of the L-methionine exporter BrnFE from *Corynebacterium glutamicum,*
26) overexpressed polynucleotide which codes for one or more components of the valine exporter YgaZH from *Escherichia coli* (b2682, b2683),
27) overexpressed polynucleotide which codes for the putative transporter YjeH from *Escherichia coli* (b4141),
28) overexpressed polynucleotide which codes for one or more components of the pyridine nucleotide transhydrogenase PntAB (EC 1.6.1.2),
29) overexpressed polynucleotide which codes for an O-succinylhomoserine sulfhydrylase MetZ (EC 2.5.1.48),
30) overexpressed polynucleotide which codes for a phosphoenolpyruvate carboxylase Pyc (EC 4.1.1.31).

Preferred features here are one or more chosen from the group:
1) overexpressed polynucleotide which codes for one or more components of the thiosulphate/sulphate transport system CysPUWA (EC 3.6.3.25),
2) overexpressed polynucleotide which codes for a 3'-phosphoadenosine 5'-phosphosulphate reductase CysH (EC 1.8.4.8),
3) overexpressed polynucleotide which codes for one or more components of the sulphite reductase CysJI (EC 1.8.1.2),
4) overexpressed polynucleotide which codes for a cysteine synthase A CysK (EC 2.5.1.47),
5) overexpressed polynucleotide which codes for a cysteine synthase B CysM (EC 2.5.1.47),
6) overexpressed polynucleotide which codes for a serine acetyltransferase CysE (EC 2.3.1.30),
7) overexpressed polynucleotide which codes for one or more components of the glycine cleavage system GcvTHP-Lpd (EC 2.1.2.10, EC 1.4.4.2, EC 1.8.1.4),
8) overexpressed polynucleotide which codes for a lipoyl synthase LipA (EC 2.8.1.8),
9) overexpressed polynucleotide which codes for a lipoyl protein ligase LipB (EC 2.3.1.181),
10) overexpressed polynucleotide which codes for a phosphoglycerate dehydrogenase SerA (EC 1.1.1.95),
11) overexpressed polynucleotide which codes for a 3-phosphoserine phosphatase SerB (EC 3.1.3.3),
12) overexpressed polynucleotide which codes for a 3-phosphoserine/phosphohydroxythreonine aminotransferase SerC (EC 2.6.1.52),
13) overexpressed polynucleotide which codes for a serine hydroxymethyltransferase GlyA (EC 2.1.2.1),
14) overexpressed polynucleotide which codes for an aspartokinase I and homoserine dehydrogenase I ThrA (EC 2.7.2.4, EC 1.1.1.3),
15) overexpressed polynucleotide which codes for an aspartate kinase LysC (EC 2.7.2.4),
16) overexpressed polynucleotide which codes for a homoserine dehydrogenase Hom (EC 1.1.1.3),
17) overexpressed polynucleotide which codes for a homoserine acetyltransferase MetX (EC 2.3.1.31),
18) overexpressed polynucleotide which codes for a homoserine O-transsuccinylase MetA (EC 2.3.1.46),
19) overexpressed polynucleotide which codes for a cystathionine gamma-synthase MetB (EC 2.5.1.48),
20) overexpressed polynucleotide which codes for a β-C—S-lyase AecD (EC 4.4.1.8, also called beta-lyase),
21) overexpressed polynucleotide which codes for a cystathionine beta-lyase MetC (EC 4.4.1.8),
22) overexpressed polynucleotide which codes for a B12-independent homocysteine S-methyltransferase MetE (EC 2.1.1.14),
23) overexpressed polynucleotide which codes for a B12-dependent homocysteine S-methyltransferase MetH (EC 2.1.1.13),
24) overexpressed polynucleotide which codes for a methylenetetrahydrofolate reductase MetF (EC 1.5.1.20).

Very particularly preferred features here are chosen from the group:
1) overexpressed polynucleotide which codes for an aspartokinase I and homoserine dehydrogenase I ThrA (EC 2.7.2.4, EC 1.1.1.3),
2) overexpressed polynucleotide which codes for an aspartate kinase LysC (EC 2.7.2.4),
3) overexpressed polynucleotide which codes for a homoserine dehydrogenase Hom (EC 1.1.1.3),
4) overexpressed polynucleotide which codes for a homoserine acetyltransferase MetX (EC 2.3.1.31),
5) overexpressed polynucleotide which codes for a homoserine O-transsuccinylase MetA (EC 2.3.1.46),
6) overexpressed polynucleotide which codes for a cystathionine gamma-synthase MetB (EC 2.5.1.48),
7) overexpressed polynucleotide which codes for a β-C—S-lyase AecD (EC 4.4.1.8, also called beta-lyase),
8) overexpressed polynucleotide which codes for a cystathionine beta-lyase MetC (EC 4.4.1.8),
9) overexpressed polynucleotide which codes for a B12-independent homocysteine S-methyltransferase MetE (EC 2.1.1.14),
10) overexpressed polynucleotide which codes for a B12-dependent homocysteine S-methyltransferase MetH (EC 2.1.1.13),
11) overexpressed polynucleotide which codes for a methylenetetrahydrofolate reductase MetF (EC 1.5.1.20).

To improve the production of L-methionine in *C. glutamicum*, it may be expedient to attenuate one or more genes chosen from the group of:
a) a gene pgi coding for glucose 6-phosphate isomerase (Pgi, EC no. 5.3.1.9),
b) a gene thrB coding for homoserine kinase (ThrB, EC no. 2.7.1.39),
c) a gene metK coding for S-adenosylmethionine synthase (MetK, EC no. 2.5.1.6),
d) a gene dapA coding for dihydrodipicolinate synthase (DapA, EC no. 4.2.1.52),
e) a gene pck coding for phosphoenolpyruvate carboxykinase (Pck, EC no. 4.1.1.49),
f) a gene cg3086 coding for cystathionine γ-lyase (Cg3086, EC no. 4.4.1.1),
g) a gene cg2344 coding for cystathionine β-synthase (Cg2344, EC no. 4.2.1.22),
h) a gene cg3031 coding for the regulator protein Cg3031, i) a gene mcbR coding for the transcription regulator of L-methionine biosynthesis (McbR),
j) a gene metQ coding for a subunit of the L-methionine transporter (MetQNI),
k) a gene metN coding for a subunit of the L-methionine transporter (MetQNI),
l) a gene metI coding for a subunit of the L-methionine transporter (MetQNI),
m) a gene metP coding for the L-methionine transporter (MetP).

To improve the production of L-methionine in E. coli, it may be expedient to attenuate one or more genes chosen from the group of:
a) a gene metJ (b3938, ECK3930) coding for the transcription regulator of L-methionine biosynthesis (MetJ),
b) a gene pgi (b4025, ECK4017) coding for glucose 6-phosphate isomerase (Pgi, EC no. 5.3.1.9),
c) a gene thrB (b0003, ECK0003) coding for homoserine kinase (ThrB, EC no. 2.7.1.39),
d) a gene metK (b2942, ECK2937) coding for S-adenosylmethionine synthase (MetK, EC no. 2.5.1.6),
e) a gene dapA (b2478, ECK2474) coding for dihydrodipicolinate synthase (DapA, EC no. 4.2.1.52),
f) a gene pck (b3403, ECK3390) coding for phosphoenolpyruvate carboxykinase (Pck, EC no. 4.1.1.49),
g) a gene purU (b1232, ECK1227) coding for formyltetrahydrofolate hydrolase (PurU, EC no. 3.5.1.10),
h) a gene pykA (b1854, ECK1855) coding for pyruvate kinase II (PykA, EC no. 2.7.1.40),
i) a gene pykF (b1676, ECK1672) coding for pyruvate kinase I (PykF, EC no. 2.7.1.40),
j) a gene metQ (b0197, ECK0197) coding for a subunit of the L-methionine transporter (MetQNI),
k) a gene metI (b0198, ECK0198) coding for a subunit of the L-methionine transporter (MetQNI),
l) a gene metN (b0199, ECK0199) coding for a subunit of the L-methionine transporter (MetQNI),
m) a gene dcd (b2065, ECK2059) coding for deoxycytidine 5'-triphosphate deaminase (Dcd, EC no. 3.5.4.13),
n) a gene yncA (b1448, ECK1442) coding for putative N-acyltransferase (YncA, Metabolic Explorer WO2010/020681),
o) a gene fnrS (b4699, ECK4511) coding for the regulatory sRNA FnrS.

BRIEF DESCRIPTION OF THE DRAWING

FIG. 1 schematically shows the pMA-RDL2 plasmid. AmpR: Ampicillin resistance gene; codes for beta-lactamase, upstream: SEQ ID NO: 6; contains recognition sequences for the restriction enzymes PadI and FseI and a ribosome binding site, RDL2: Sequence of the gene RDL2 from Saccharomyces cerevisiae S288c, downstream: SEQ ID NO: 7; contains a second stop codon TAA followed by the T1 terminator of the rnpB gene from E. coli MG1655. Recognition sequences for the restriction enzymes PmeI and SbfI follow after this.

DETAILED DESCRIPTION OF THE INVENTION

The invention relates to a process for the fermentative preparation of sulphur-containing amino acids chosen from the group of L-methionine, L-cysteine, L-cystine, L-homocysteine and L-homocystine. The process is carried out with a microorganism of the family Enterobacteriaceae or with a microorganism of the family Corynebacteriaceae which overexpresses a gene coding for a polypeptide with the enzymatic activity of a thiosulphate sulphurtransferase.

The term "gene" here means a section on the deoxyribonucleic acid (DNA) which contains the information for the production (transcription) first of a ribonucleic acid (RNA), and this the information for the production (translation) of a protein (polypeptide), here a polypeptide with the activity of a thiosulphate sulphurtransferase. The fact that a gene or a polynucleotide contains the information for production of a protein is also called coding of a protein or polypeptide by the gene or by the RNA. Endogenous genes or polynucleotides are understood as meaning the open reading frames (ORF), genes or alleles or polynucleotides thereof present in the population of a species. The terms "gene" and "ORF" (open reading frame) are used synonymously in this invention.

The term "polynucleotide" in general relates to polyribonucleotides and polydeoxyribonucleotides, which can be non-modified RNA or DNA or modified RNA or DNA.

The term "polypeptide" indicates peptides or proteins which contain two or more amino acids joined via peptide bonds. The terms polypeptide and protein are used as synonyms. Proteins belong to the base units of all cells. They not only impart structure to the cell, but are the molecular "machines" which transport substances, catalyse chemical reactions and recognize signal substances.

"Proteinogenic amino acids" are understood as meaning the amino acids which occur in natural proteins, that is to say in proteins of microorganisms, plants, animals and humans. These include, in particular, L-amino acids chosen from the group of L-aspartic acid, L-asparagine, L-threonine, L-serine, L-glutamic acid, L-glutamine, glycine, L-alanine, L-cysteine, L-valine, L-methionine, L-isoleucine, L-leucine, L-tyrosine, L-phenylalanine, L-histidine, L-lysine, L-tryptophan, L-proline and L-arginine, as well as selenocysteine. In this context, the proteinogenic amino acids are always α-amino acids. Apart from the amino acid glycine, for all proteinogenic amino acids the α-carbon atom is asymmetric (the molecules are chiral): Two enantiomers of each of these amino acids exist. In this context, only one of the two enantiomers is proteinogenic, and in fact the L-amino acid: the apparatus necessary for building up the proteins—the ribosome, the tRNA, the aminoacyl-tRNA synthetase (this loads the tRNA with amino acids) and others—are themselves also chiral and can recognize only the L-variants.

The term "gene expression" ("expression" for short) in general indicates the expression of the genetic information to form a phenotype. In the narrower sense, gene expression indicates the transcription of a gene to an RNA and the subsequent translation of the RNA to a polypeptide, which may have an enzymatic activity.

The term "overexpression" is understood generally as meaning an increase in the intracellular concentration or activity of a ribonucleic acid, a protein or an enzyme compared with the starting strain (parent strain) or wild-type strain. In the case of the present invention, thiosulphate sulphurtransferase genes or polynucleotides which code for a thiosulphate sulphurtransferase polypeptide are overexpressed.

A "starting strain" (parent strain) is understood as meaning the microorganism strain on which measures to increase the productivity of one or more amino acids, peptides or proteins, or measures to increase the activity of one or more enzymes (e.g. a measure leading to overexpression) are performed. A starting strain can be a wild-type strain, but also a strain which has already been modified previously (for example a production strain).

A "wild type" of a cell preferably indicates a cell whose genome is in a state such as is formed naturally by evolution. The term is used both for the entire cell and for individual genes. Thus in particular those cells or those genes whose gene sequences have been at least partly modified by humans by means of recombinant methods do not fall under the term "wild type".

The mutants obtained in the context of this invention show an increased secretion or production of the desired amino acid in a fermentation process compared with the starting strain or parent strain employed. In this context, the amino acids are released into the medium surrounding them or are accumulated inside the cell (accumulation).

The term "increase" or "increased activity" in this connection describes the increase in the intracellular enzymatic activity of one or more enzymes in a microorganism which are coded by the corresponding DNA.

In principle, an increase in the enzymatic activity can be achieved, for example, by increasing the number of copies of the gene sequence or gene sequences which code for the enzyme, using a potent promoter or using a gene or allele which codes for a corresponding enzyme with an increased activity, and optionally combining these measures. Cells which have been genetically modified according to the invention are produced, for example, by transformation, transduction, conjugation or a combination of these methods with a vector which contains the desired gene, an allele of this gene or parts thereof and a vector which renders possible expression of the gene. Heterologous expression is achieved in particular by integration of the gene or the alleles into the chromosome of the cell or an extrachromosomally replicating vector.

An overview of the possibilities of increasing the enzymatic activity in cells by the example of pyruvate carboxylase is given in DE-A-100 31 999 which is incorporated herewith by reference and the disclosure content of which with respect to the possibilities for increasing the enzymatic activity in cells forms a part of the disclosure of the present invention.

The increase in enzymatic activity can be achieved, for example, by increasing the number of copies of the corresponding polynucleotides chromosomally or extrachromosomally by at least one copy.

A widely used method for increasing the number of copies comprises incorporating the corresponding polynucleotide into a vector, preferably a plasmid, which is replicated by a bacterium.

Suitable plasmid vectors for Enterobacteriaceae are e.g. cloning vectors derived from pACYC184 (Bartolomé et al.; Gene 102: 75-78 (1991)), pTrc99A (Amann et al.; Gene 69: 301-315 (1988)) or pSC101 derivatives (Vocke and Bastia; Proceedings of the National Academy of Sciences USA 80(21): 6557-6561 (1983)). Plasmids derived from pCL1920 (Lerner, C. G. and Inouye, M., Nucl. Acids Res. (1990) 18:4631[PMID: 2201955]) are furthermore particularly suitable. Plasmid vectors derived from bacterial artificial chromosomes (BAC), such as e.g. pCC1BAC (EPICENTRE Biotechnologies, Madison, USA), are likewise suitable for increasing the number of copies of the corresponding polynucleotides in E. coli.

Suitable plasmid vectors for C. glutamicum are, for example, pZ1 (Menkel et al., Applied and Environmental Microbiology 64: 549-554 (1989)), pEKEx1 (Eikmanns et al., Gene 107: 69-74 (1991)) or pHS2-1 (Sonnen et al., Gene 107: 69-74 (1991)). They are based on the cryptic plasmids pHM1519, pBL1 or pGA1. Other plasmid vectors, such as, for example, those which are based on pCG4 (U.S. Pat. No. 4,489,160) or pNG2 (Serwold-Davis et al., FEMS Microbiology Letters 66: 119-124 (1990)) or pAG1 (U.S. Pat. No. 5,158,891), can be employed in the same manner. An overview article on the subject of plasmids in C. glutamicum is to be found in Tauch et al. (Journal of Biotechnology 104, 27-40 (2003)).

Transposons, insertion elements (IS elements) or phages can furthermore be employed as vectors. Such genetic systems are described, for example, in the patent specifications U.S. Pat. Nos. 4,822,738, 5,804,414 and 5,804,414. The IS element ISaB1 described in WO 92/02627 or the transposon Tn 45 of the plasmid pXZ10142 (referred to in "Handbook of Corynebacterium glutamicum" (editors: L. Eggeling and M. Bott)) can be used in the same manner.

Another widespread method for achieving overexpression is the method of chromosomal gene amplification. In this method, at least one additional copy of the polynucleotide of interest is inserted into the chromosome of a bacterium. Such amplification methods are described, for example, in WO 03/014330 or WO 03/040373.

A further method for achieving overexpression comprises linking the corresponding gene or allele in a functional manner (operably linked) with a promoter or an expression cassette. Suitable promoters for C. glutamicum are described, for example, in FIG. 1 of the overview article by Patek et al. (Journal of Biotechnology 104(1-3), 311-323 (2003)). The variants of the dapA promoter, for example the promoter A25, described by Vasicova et al. (Journal of Bacteriology 181, 6188-6191 (1999)), can be employed in the same manner. The gap promoter of C. glutamicum (EP 06007373) can furthermore be used.

For E. coli e.g. the promoters T3, T7, SP6, M13, lac, tac and trc described by Amann et al. (Gene 69(2), 301-315 (1988)) and Amann and Brosius (Gene 40(2-3), 183-190 (1985)) are known, some of which can also be used for C. glutamicum. Such a promoter can be inserted, for example, upstream of the gene in question, typically at a distance of approximately 1-500 nucleobases from the start codon. U.S. Pat. No. 5,939,307 reports that by incorporation of expression cassettes or promoters, such as, for example, the tac promoter, trp promoter, lpp promoter or PL promoter and PR promoter of the phage λ, for example upstream of the chromosomal threonine operon, it was possible to achieve an increase in the expression. The promoters of phage T7, the gear-box promoter or the nar promoter can be used in the same manner. Such expression cassettes or promoters can also be used to overexpress plasmid-bound genes, as described in EP 0 593 792. By using the lacIQ allele, expression of plasmid-bound genes can in turn be controlled (Glascock and Weickert, Gene 223, 221-231 (1998)). It is furthermore possible for the activity of the promoters to be increased by modification of their sequence by means of one or more nucleotide exchanges, by insertion(s) and/or deletion(s).

By the measures of overexpression, the activity or concentration of the corresponding polypeptide is in general increased by at least 10%, 25%, 50%, 75%, 100%, 150%, 200%, 300%, 400% or 500%, by a maximum of up to 1,000% or 2,000%, based on the activity or concentration of the polypeptide in the corresponding starting strain (wild type or starting microorganism) before the measure leading to overexpression.

Methods for determination of the enzymatic activity of thiosulphate sulphurtransferases are described, for example, by Cheng H, Donahue J L, Battle S E, Ray W K, Larson T J, 2008, Open Microbiol J., 2:18-28 and by Alexander K., Volini M, 1987, J. Biol. Chem., 262: 6595-6604.

The expression of the abovementioned enzymes or genes can be detected with the aid of 1- and 2-dimensional protein gel separation and subsequent optical identification of the protein concentration in the gel with appropriate evaluation software. If the increase in an enzyme activity is based exclusively on an increase in the expression of the corresponding gene, the increase in the enzyme activity can be quantified in a simple manner by a comparison of the 1- or 2-dimensional protein separations between the wild type and the genetically modified cell. A conventional method for preparation of the protein gels in the case of bacteria and for identification of the proteins is the procedure described by Hermann et al. (Electrophoresis, 22: 1712.23 (2001)). The protein concentration can likewise be analysed by western blot hybridization with an antibody specific for the protein to be detected (Sambrook et al., Molecular Cloning: a laboratory manual, 2nd ed. Cold Spring Harbor Laboratory Press, Cold Spring Harbor, N.Y. USA, 1989) and subsequent optical evaluation with appropriate software for determination of the concentration (Lohaus and Meyer (1989) Biospektrum, 5: 32-39; Lottspeich (1999), Angewandte Chemie 111: 2630-2647). The activity of DNA-binding proteins can be measured by means of DNA band shift assays (also called gel retardation; Wilson et al. (2001) Journal of Bacteriology, 183: 2151-2155). The action of DNA-binding proteins on the expression of other genes can be detected by various well-described methods of reporter gene assay (Sambrook et al., Molecular Cloning: a laboratory manual, 2nd ed. Cold Spring Harbor Laboratory Press, Cold Spring Harbor, N.Y. USA, 1989). The intracellular enzymatic activities can be determined by various methods which have been described (Donahue et al. (2000) Journal of Bacteriology 182 (19): 5624-5627; Ray et al. (2000) Journal of Bacteriology 182 (8): 2277-2284; Freedberg et al. (1973) Journal of Bacteriology 115 (3): 816-823). If no concrete methods for determination of the activity of a particular enzyme are given in the following, the determination of the increase in enzyme activity and also the determination of the reduction in an enzyme activity are preferably carried out by means of the methods described in Hermann et al., Electophoresis, 22: 1712-23 (2001), Lohaus et al., Biospektrum 5 32-39 (1998), Lottspeich, Angewandte Chemie 111: 2630-2647 (1999) and Wilson et al., Journal of Bacteriology 183: 2151-2155 (2001).

If the increase in enzyme activity is effected by mutation of the endogenous gene, such mutations can be generated either by conventional methods in a non-targeted manner, such as, for example, by UV irradiation or by mutation-inducing chemicals, or in a targeted manner by means of genetic engineering methods, such as deletion(s), insertion(s) and/or nucleotide exchange(s). Genetically modified cells are obtained by these mutations. Particularly preferred mutants of enzymes are in particular also those enzymes which can no longer be feedback-inhibited, or at least can be feedback-inhibited to a lesser extent compared with the wild-type enzyme.

If the increase in enzyme activity is effected by increasing the expression of an enzyme, the number of copies, for example, of the corresponding genes is increased or the promoter and regulation region or the ribosome binding site upstream of the structural gene are mutated. Expression cassettes which are incorporated upstream of the structural gene act in the same manner. By inducible promoters it is additionally possible to increase the expression at any desired point in time. Furthermore, however, so-called enhancers can be assigned to the enzyme gene as regulatory sequences, which likewise have the effect of an increased gene expression via an improved interaction between the RNA polymerase and DNA. The expression is likewise improved by measures for prolonging the life of the mRNA. The enzyme activity is furthermore likewise increased by preventing degradation of the enzyme protein. In this context, the genes or gene constructs are either present in plasmids with a different number of copies, or are integrated in the chromosome and amplified. Alternatively, an overexpression of the genes in question can furthermore be achieved by modifying the media composition and culture procedure. Instructions on this are to be found by the person skilled in the art inter alia in Martin et al. (Bio/Technology 5, 137-146 (1987)), in Guerrero et al. (Gene 138, 35-41 (1994)), Tsuchiya and Morinaga (Bio/Technology 6, 428-430 (1988)), in Eikmanns et al. (Gene 102, 93-98 (1991)), in EP-A-0 472 869, in U.S. Pat. No. 4,601,893, in Schwarzer and Pühler (Bio/Technology 9, 84-87 (1991)), in Reinscheid et al. (Applied and Environmental Microbiology 60, 126-132 (1994)), in LaBarre et al. (Journal of Bacteriology 175, 1001-1007 (1993)), in WO-A-96/15246, in Malumbres et al. (Gene 134, 15-24 (1993)), in JP-A-10-229891, in Jensen and Hammer (Biotechnology and Bioengineering 58, 191-195 (1998)) and in known textbooks of genetics and molecular biology. The measures described above, like the mutations, lead to genetically modified cells.

Those plasmid vectors with the aid of which the method of gene amplification by integration into the chromosome can be used are furthermore also suitable, such as has been described, for example, by Reinscheid et al. (Applied and Environmental Microbiology 60: 126-132 (1994)) for duplication or amplification of the hom-thrB operon. In this method, the complete gene is cloned into a plasmid vector which can be replicated in a host (typically *Escherichia coli*), but not in *Corynebacterium glutamicum*. Possible vectors are, for example, pSUP301 (Simon et al., Bio/Technology 1: 784-791 (1983)), pK18mob or pK19mob (Schafer et al., Gene 145: 69-73 (1994)), pGEM-T (Promega Corporation, Madison, Wis., USA), pCR2.1-TOPO (Shuman, Journal of Biological Chemistry 269: 32678-84 (1994)), pCR-BluntII-TOPO (Invitrogen, Groningen, The Netherlands), pEM1 (Schrumpf et al., Journal of Bacteriology 173: 4510-4516)) or pBGS8 (Spratt et al., Gene 41: 337-342 (1986)). The plasmid vector which contains the gene to be amplified is then converted into the desired strain of *Corynebacterium glutamicum* by conjugation or transformation. The method of conjugation is described, for example, by Schafer et al., Applied and Environmental Microbiology 60: 756-759 (1994). Methods for transformation are described, for example, by Thierbach et al., Applied Microbiology and Biotechnology 29: 356-362 (1988), Dunican and Shivnan, Bio/Technology 7: 1067-1070 (1989) and Tauch et al., FEMS Microbiology Letters 123: 343-347 (1994). After homologous recombination by means of a cross-over event, the resulting strain contains at least two copies of the gene in question. A similar method for *E. coli* is described, for example, by Link, A. J., Phillips, D. and Church, G. M. (1997), J. Bacteriology 179: 6228-6237.

For insertion or deletion of DNA in the chromosome, recombinase-mediated methods can also be used, such as have been described, for example, by Datsenko K A, Wanner B L., 2000, Proc Natl Acad Sci USA., 97(12):6640-5.

The wording "an activity of an enzyme which is increased compared with its wild-type strain or starting strain" used above and in the following is preferably always to be understood as meaning an activity of the particular enzyme which has been increased by a factor of at least 2, particularly preferably of at least 10, moreover preferably of at least 100, moreover still more preferably of at least 1,000 and most preferably of at least 10,000. The cell according to the invention which has "an activity of an enzyme which is increased compared with its wild-type strain or starting strain" furthermore also includes in particular a cell whose wild type or starting strain has no or at least no detectable activity of this enzyme and which shows a detectable activity of this enzyme only after increasing the enzyme activity, for example by overexpression. In this connection, the term "overexpression" or the wording "increase in expression" used in the following also includes the case where a starting cell, for example a wild-type cell, has no or at least no detectable expression and a detectable expression of the enzyme is induced only by recombinant methods.

The isolated bacteria obtained by the measures of the invention show an increased secretion or production of the desired amino acid in a fermentation process compared with the starting strain or parent strain employed.

Isolated bacteria are to be understood as meaning the mutants and recombinant bacteria according to the invention which have been isolated or produced, in particular of the Enterobacteriaceae or Corynebacteriaceae family, and which have an increased activity of a thiosulphate sulphurtransferase compared with the starting strain.

The output of the bacteria isolated and of the fermentation process using the same with respect to one or more of the parameters chosen from the group of product concentration (product per volume), product yield (product formed per carbon source consumed) and product formation (product formed per volume and time), or also other process parameters and combinations thereof, is improved by at least 0.5%, at least 1%, at least 1.5% or at least 2%, based on the starting strain or parent strain or the fermentation process using the same.

In the process according to the invention, the bacteria can be cultivated continuously—as described, for example, in PCT/EP2004/008882—or discontinuously in the batch process (batch cultivation) or in the fed batch (feed process) or repeated fed batch process (repetitive feed process) for the purpose of production of L-amino acids. A summary of a general nature of known cultivation methods is available in the textbook by Chmiel (Bioprozesstechnik 1. Einführung in die Bioverfahrenstechnik (Gustav Fischer Verlag, Stuttgart, 1991)) or in the textbook by Storhas (Bioreaktoren and periphere Einrichtungen (Vieweg Verlag, Braunschweig/Wiesbaden, 1994)).

The culture medium or fermentation medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981). The terms culture medium and fermentation medium or medium are mutually interchangeable.

Sugars and carbohydrates, such as e.g. glucose, sucrose, lactose, fructose, maltose, molasses, sucrose-containing solutions from sugar beet or cane sugar production, starch, starch hydrolysate and cellulose, oils and fats, such as, for example, soya oil, sunflower oil, groundnut oil and coconut fat, fatty acids, such as, for example, palmitic acid, stearic acid and linoleic acid, alcohols, such as, for example, glycerol, methanol and ethanol, and organic acids, such as, for example, acetic acid, can be used as the source of carbon. These substances can be used individually or as a mixture.

Organic nitrogen-containing compounds, such as peptones, yeast extract, meat extract, malt extract, corn steep liquor, soya bean flour and urea, or inorganic compounds, such as ammonium sulphate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. According to the invention, the source of sulphur employed is a salt of dithiosulphuric acid (thiosulphate), optionally together with other sources of sulphur, such as, for example, sulphate, sulphite or dithionite.

The culture medium must furthermore contain salts, for example in the form of chlorides, of metals, such as, for example, sodium, potassium, magnesium, calcium and iron, such as, for example, magnesium sulphate or iron sulphate, which are necessary for growth. Finally, essential growth substances, such as amino acids, for example homoserine, and vitamins, for example thiamine, biotin or pantothenic acid, can be employed in addition to the above-mentioned substances.

Suitable precursors of the particular amino acid can moreover be added to the culture medium.

The starting substances mentioned can be added to the culture in the form of a single batch, or can be fed in during the cultivation in a suitable manner.

Basic compounds, such as sodium hydroxide, potassium hydroxide, ammonia or aqueous ammonia, or acid compounds, such as phosphoric acid or sulphuric acid, can be employed in a suitable manner to control the pH of the culture. The pH is in general adjusted to a value of from 6.0 to 9.0, preferably 6.5 to 8. Antifoams, such as, for example, fatty acid polyglycol esters, can be employed to control the development of foam. Suitable substances having a selective action, such as, for example, antibiotics, can be added to the medium to maintain the stability of plasmids. To maintain aerobic conditions, oxygen or oxygen-containing gas mixtures, such as, for example, air, are introduced into the culture. The use of liquids which are enriched with hydrogen peroxide is likewise possible. The fermentation is optionally carried out under increased pressure, for example under a pressure of from 0.03 to 0.2 MPa. The temperature of the culture is usually 20° C. to 45° C., and preferably 25° C. to 40° C. In the batch process the cultivation is continued until a maximum of the desired amino acid has formed. This target is usually reached within 10 hours to 160 hours. In continuous processes longer cultivation times are possible.

Suitable fermentation media are described, inter alia, in U.S. Pat. No. 6,221,636, in U.S. Pat. No. 5,840,551, in U.S. Pat. No. 5,770,409, in U.S. Pat. No. 5,605,818, in U.S. Pat. No. 5,275,940 and in U.S. Pat. No. 4,224,409.

Methods for the determination of L-amino acids are known from the prior art. The analysis can be carried out, for example, as described by Spackman et al. (Analytical Chemistry, 30, (1958), 1190) by ion exchange chromatography with subsequent ninhydrin derivatization, or it can be carried out by reversed phase HPLC, as described by Lindroth et al. (Analytical Chemistry (1979) 51: 1167-1174).

The fermentation broth produced in this manner is then further processed to a solid or liquid product.

A fermentation broth is understood as meaning a fermentation medium in which a microorganism has been cultivated for a certain time and at a certain temperature. The fermentation medium and/or the medium employed during the fermentation contain(s) all the substances and components which ensure a multiplication of the microorganism and a formation of the desired amino acid.

At the conclusion of the fermentation, the fermentation broth formed accordingly contains a) the biomass of the microorganism formed as a result of the multiplication of the cells of the microorganism, b) the desired amino acid formed in the course of the fermentation, c) the organic by-products formed in the course of the fermentation and d) the constituents of the fermentation medium/fermentation media employed or of the starting substances which have not been consumed by the fermentation, such as, for example, vitamins, such as biotin, amino acids, such as homoserine, or salts, such as magnesium sulphate.

The organic by-products include substances which are possibly produced, in addition to the particular desired L-amino acid, and possibly secreted by the microorganisms employed in the fermentation. These include L-amino acids which make up less than 30%, 20% or 10%, compared with the desired amino acid. They furthermore include organic acids which carry one to three carboxyl groups, such as, for example, acetic acid, lactic acid, citric acid, malic acid or fumaric acid. Finally, they also include sugars, such as, for example, trehalose.

Typical fermentation broths which are suitable for industrial purposes have an amino acid content of from 40 g/kg to 180 g/kg or 50 g/kg to 150 g/kg. The content of biomass (as dried biomass) is in general 20 to 50 g/kg.

EXAMPLES

Example 1

Synthesis and Cloning of the Gene RDL2

For the expression of the ORF RDL2 (SEQ ID NO: 1) from S. cerevisiae, a nucleotide sequence (GENEART AG; Regensburg, Germany) which comprises an upstream sequence ("upstream", SEQ ID NO: 6), the sequence of ORF RDL2 ("RDL2", SEQ ID NO: 1) and a downstream sequence ("downstream", SEQ ID NO: 7) was synthesized de novo. The upstream sequence contains recognition sequences for the restriction enzymes PadI and FseI and a ribosome binding site. The downstream sequence contains a second stop codon TAA followed by the T1 terminator of the rnpB gene from E. coli MG1655. Recognition sequences for the restriction enzymes PmeI and SbfI follow after this. After the synthesis, the nucleotide sequence was cleaved with SacI and KpnI and cloned into the plasmid pMA (ampR), likewise cleaved with SacI and KpnI. The resulting plasmid was designated "pMA-RDL2" (SEQ ID NO: 8, FIG. 1).

Starting from the amino acid sequence of the protein Rdl2p coded by the ORF RDL2 (sequence "RDL2p", SEQ ID NO: 2), three different DNA sequences which code for Rdl2p proteins with the wild-type amino acid sequence were generated. The sequences were designated "RDL2a" (SEQ ID NO: 3), "RDL2b" (SEQ ID NO: 4) and "RDL2c" (SEQ ID NO: 5). These three sequences were each synthesized de novo together with the upstream and downstream sequences described above and cloned into the plasmid pMA as described above (GENEART AG; Regensburg, Germany). The resulting plasmids were designated pMA-RDL2a, pMA-RDL2b and pMA-RDL2c. The variants mentioned differ in the optimization of the codon usage of the microorganism used for the process. The values for the adaptation to the codon usage are thus as follows:

RDL2: Codon usage not adapted (codon adaptation index CAI=0.27)

RDL2a: Codon usage slightly adapted to E. coli (CAI=0.38)

RDL2b: Codon usage more highly adapted to E. coli (CAI=0.72)

RDL2c: Codon usage completely adapted to E. coli (CAI=1)

Example 2

Cloning of the ORFs RDL2, RDL2a, RDL2b and RDL2c into the Plasmid pME101-thrA*1-cysE-Pgap-metA*11

For the expression in E. coli, the four gene variants coding for the RDL2 protein were each cloned into the E. coli production plasmid pME101-thrA*1-cysE-Pgap-metA*11 (WO2007/077041) downstream of metA*11.

For this, the genes were each amplified with the primers RDL2-t-4-f (SEQ ID NO: 11) and RDL2-r (SEQ ID NO: 12) using the polymerase chain reaction (PCR) with Phusion DNA Polymerase (Finnzymes Oy, Espoo, Finland). The plasmids pMA-RDL2, pMA-RDL2a, pMA-RDL2b and pMA-RDL2c from Example 1 served as templates.

```
RDL2-t4-f (SEQ ID NO: 11):
5' aggacagtcgacggtaccgcaagcttcggcttcgcACTGGAAAGCGGGCAGTGAG 3'

RDL2-r (SEQ ID NO: 12):
5' AGCGCGACGTAATACGACTC 3'
```

The PCR products 804 bp in size and the plasmid pME101-thrA*1-cysE-PgapA-metA*11 were cleaved with the restriction enzymes SalI and SbfI, ligated and transformed into the E. coli strain DH5α. Plasmid-carrying cells were selected by cultivation on LB agar with 50 µg/ml of streptomycin. After isolation of the plasmid DNA, successful cloning was detected by control cleavage with the restriction enzyme AgeI. Finally, the cloned DNA fragments were sequenced with the following primers:

```
pME-RDL2-Seqf (SEQ ID NO: 13):
5' ATGTGGAAGCCGGACTAGAC 3' pME-RDL2-Seqr (SEQ ID NO: 14):
5' TCGGATTATCCCGTGACAGG 3'
```

The plasmids formed in this way were designated pME-RDL2, pME-RDL2a, pME-RDL2b and pME-RDL2c.

Example 3

Transformation of E. coli MG1655ΔmetJ Ptrc-metH Ptrc-metF PtrcF-cysPUWAM PtrcF-cysJIH Ptrc09-gcvTHP The E. coli strain MG1655ΔmetJ metA*11 Ptrc-metH Ptrc-metF PtrcF-cysPUWAM PtrcF-cysJIH (designated DM2219 in the following) which produces L-methionine is described in the patent specification WO 2009/043803 A2.

The strain was transformed in each case with the plasmids pME-RDL2, pME-RDL2a, pME-RDL2b and pME-RDL2c and with the plasmid pME101-thrA*1-cysE-PgapA-metA*11 (WO2009/043803 A2) and plasmid-carrying cells were selected on LB agar with 50 µg/ml of streptomycin. The transformants were transinoculated into in each case 10 ml of LB liquid medium with 1% glucose and 50 µg/ml of streptomycin and were cultivated at 37° C. for 16 hours. Glycerol was then added to a final concentration of 10% and the cultures were frozen at −70° C.

Example 4

Evaluation of the E. Coli L-Methionine Production Strains

The output capacity of the E. coli L-methionine production strains was evaluated by production experiments in 100 ml conical flasks. As precultures, in each case 10 ml of preculture medium (10% LB medium with 2.5 g/l of glucose and 90% PC1 minimal medium) were inoculated with 100 µl of cell culture and the cultures were cultivated at 37° C. for hours. In each case 10 ml of PC1 minimal medium (Table 1) were then inoculated with these to an OD 600 nm of 0.2 (Eppendorf Bio-Photometer; Eppendorf A G, Hamburg, Germany) and cultivated at 37° C. for 24 hours. The extracellular L-methionine concentration was determined with an amino acid analyzer (Sykam GmbH, Eresing, Germany) by ion exchange chromatography and post-column derivatization with ninhydrin detection. The extracellular glucose concentration was determined with a YSI 2700 Select Glucose Analyzer (YSI Life Sciences, Yellow Springs, Ohio, USA). The data show that the expression of ORF RDL2, RDL2a, RDL2b or RDL2c significantly increases the L-methionine concentration (Table 2).

TABLE 1

PC1 minimal medium

| Substance | Concentration |
| --- | --- |
| $ZnSO_4 * 7 H_2O$ | 4 mg/l |
| $CuCl_2 * 2 H_2O$ | 2 mg/l |
| $MnSO_4 * H_2O$ | 20 mg/l |
| $CoCl_2 * 6 H_2O$ | 8 mg/l |
| $H_3BO_3$ | 1 mg/l |
| $Na_2MoO_4 * 2 H_2O$ | 0.4 mg/l |
| $MgSO_4 * 7 H_2O$ | 1 g/l |
| Citric acid * 1 $H_2O$ | 6.56 g/l |
| $CaCl_2 * 2 H_2O$ | 40 mg/l |
| $K_2HPO_4$ | 8.02 g/l |
| $Na_2HPO_4$ | 2 g/l |
| $(NH_4)_2HPO_4$ | 8 g/l |
| $NH_4Cl$ | 0.13 g/l |
| $(NH_4)_2SO_3$ | 5.6 g/l |
| MOPS | 5 g/l |
| NaOH 10M | adjusted to pH 6.8 |
| $FeSO_4 * 7 H_2O$ | 40 mg/l |
| Thiamine hydrochloride | 10 mg/l |
| Vitamin B12 | 10 mg/l |
| Glucose | 10 g/l |
| Isopropyl thio-β-galactoside (IPTG) | 2.4 mg/l |
| Spectinomycin | 50 mg/l |

TABLE 2

L-Methionine concentrations in the fermentation broths of the various plasmid-carrying E. coli DM2219 strains

| Strain | Plasmid | OD (600 nm) | L-Methionine (g/l) |
| --- | --- | --- | --- |
| DM2219 | pME101-thrA*1-cysE-PgapA-metA*11 | 7.51 | 0.43 |
| DM2219 | pME-RDL2 | 7.59 | 0.51 |
| DM2219 | pME-RDL2a | 7.72 | 0.53 |
| DM2219 | pME-RDL2b | 7.50 | 0.52 |
| DM2219 | pME-RDL2c | 7.64 | 0.54 |

Example 5

Cloning of the ORFs RDL2, RDL2a, RDL2b and RDL2c into the Plasmid pEC-XT99A

As the base vector for expression of the ORFs RDL2, RDL2a, RDL2b and RDL2c in C. glutamicum, the E. coli-C. glutamicum shuttle expression plasmid pEC-XT99A (EP1085094B1) was used. The plasmids pMA-RDL2, pMA-RDL2a, pMA-RDL2b and pMA-RDL2c from Example 1 were each cleaved with the restriction enzymes StuI and NaeI and separated in a 0.8% strength agarose gel. The DNA fragments 638 bp in size were cut out of the gel and the DNA was extracted (QIAquick Gel Extraction Kit, QIAGEN, Hilden, Germany). The expression plasmid pEC-XT99A was cleaved with the restriction enzyme Ecl13611. Ligation was then in each case carried out with the DNA fragments 638 bp in size using the Ready-To-Go Ligation Kit (Amersham GE Healthcare Europe GmbH, Freiburg, Germany). The E. coli strain DH5α (Invitrogen GmbH; Darmstadt; Germany) was transformed with the ligation batches and plasmid-carrying cells were selected on LB agar with 5 µg/ml of tetracycline.

After isolation of the plasmid DNA, successful cloning was detected by a control cleavage with the restriction enzymes PmeI and SacII. Finally, the plasmids were sequenced with the following primers:

```
pECf (SEQ ID NO: 9):
5' TACTGCCGCCAGGCAAATTC 3' pECr (SEQ ID NO: 10):
5' TTTGCGCCGACATCATAACG 3'
```

The plasmid constructs in which the plasmid's own trc promoter and the ORFs coding for RDL2 have the same orientation were designated as follows: pEC-RDL2, pEC-RDL2a, pEC-RDL2b and pEC-RDL2c.

Example 6

Transformation of C. Glutamicum M1179

The strain Corynebacterium glutamicum M1179 is an ethionine-resistant producer of L-methionine (WO2007/011939). It was deposited at the Deutsche Sammlung für Mikroorganismen und Zellkulturen (DSMZ, Braunschweig, Germany) on 18.5.2005 as DSM17322 under the terms of the Budapest Treaty.

The plasmids pEC-RDL2, pEC-RDL2a, pEC-RDL2b, pEC-RDL2c and pEC-XT99A were electroporated into the strain M1179 in accordance with the electroporation conditions of Tauch et al. (1994, FEMS Microbiological Letters, 123: 343-347).

Selection of plasmid-carrying cells was performed on LB agar with 5 μg/ml of tetracycline. The plasmid DNA of the transformants was isolated (Peters-Wendisch et al., 1998, Microbiology 144, 915-927) and checked by restriction cleavage and gel electrophoresis. The strains formed in this way were designated M1179/pEC-RDL2, M1179/pEC-RDL2a, M1179/pEC-RDL2b, M1179/pEC-RDL2c and M1179/pEC-XT99A.

Example 7

Evaluation of the C. Glutamicum L-Methionine Production Strains

The C. glutamicum strains M1179.,pEC-RDL2, M1179., pEC-RDL2a, M1179.,pEC-RDL2b, M1179.,pEC-RDL2c and M1179.,pEC-XT99A produced were cultivated in a nutrient medium suitable for the production of L-methionine and the L-methionine content in the culture supernatant was determined.

For this, the strains were first smeared onto agar plates (brain-heart agar with kanamycin (25 mg/l)) and incubated at 33° C. for 24 hours. From these agar plate cultures, cells were transinoculated into in each case 10 ml of BH medium (Hirn-Herz Bouillon, Merck, Darmstadt, Germany) with mg/l of tetracycline and the cultures were shaken in 100 ml conical flasks at 33° C. and at 240 rpm for 24 hours. In each case 10 ml of PM medium (Table 3) were then inoculated with these to an OD 660 nm of 0.1 (Genios, Tecan Deutschland GmbH, Crailsheim, Germany) and cultivated at 33° C. in 100 ml conical flasks with baffles for 24 hours.

TABLE 3

| PM medium | |
| --- | --- |
| Substance | Concentration |
| Glucose | 50 g/l |
| $(NH_4)_2S_2O_3$ | 10 g/l |
| $(NH_4)Cl$ | 10 g/l |
| $MgSO_4 * 7 H_2O$ | 0.4 g/l |

TABLE 3-continued

| PM medium | |
| --- | --- |
| Substance | Concentration |
| $KH_2PO_4$ | 0.6 g/l |
| Yeast extract (Difco) | 10 g/l |
| $FeSO_4 * 7 H_2O$ | 2 mg/l |
| $MnSO_4 * H_2O$ | 2 mg/l |
| Aqueous ammonia | adjusted to pH 7.8 |
| Thiamine * HCl | 1 mg/l |
| Vitamin B12 | 0.2 mg/l |
| Biotin | 0.1 mg/l |
| Pyridoxine * HCl (vitamin B6) | 5 mg/l |
| Threonine | 238 mg/l |
| $CaCO_3$ | 50 g/l |
| Tetracycline | 5 mg/l |
| Isopropyl thio-β-galactoside (IPTG) | 1 mM |

After 24 hours the OD at 660 nm was determined (Genios, Tecan Deutschland GmbH, Crailsheim, Germany) and the concentration of L-methionine formed was measured. L-Methionine was determined with an amino acid analyzer (Sykam GmbH, Eresing, Germany) by ion exchange chromatography and post-column derivatization with ninhydrin detection. Table 4 shows the optical densities and the L-methionine concentrations of the cultures. The expression of the ORF RDL2, RDL2a, RDL2b or RDL2c results in a significant increase in the L-methionine concentration.

TABLE 4

Methionine concentrations in the fermentation broths of the various plasmid-carrying C. glutamicum M1179 strains

| Strain | OD (600 nm) | L-Methionine (g/l) |
| --- | --- | --- |
| M1179/pEC-XT99A | 25.7 | 0.47 |
| M1179/pEC-RDL2 | 25.8 | 0.50 |
| M1179/pEC-RDL2a | 24.1 | 0.50 |
| M1179/pEC-RDL2b | 26.2 | 0.55 |
| M1179/pEC-RDL2c | 24.5 | 0.54 |

The invention claimed is:

1. A recombinant microorganism selected from the group consisting of

Corynebacterium glutamicum with increased activity and/or expression of aspartate kinase and attenuation or deletion of the regulator protein McbR compared with the starting strain; and Escherichia coli with increased activity and/or expression of aspartate kinase and attenuation or deletion of the regulator protein MetJ compared with the starting strain;

wherein the recombinant microorganism secretes or produces L-methionine, and wherein the recombinant microorganism overexpresses a gene coding for a polypeptide with the activity of a thiosulphate sulphurtransferase comprising the amino acid sequence shown in SEQ ID NO: 2 or an amino acid sequence containing a deletion, substitution, insertion, addition, or combinations thereof, of from 1 to 45 amino acid residues with respect to the amino acid sequence shown in SEQ ID NO: 2, and wherein the recombinant microorganism has an increased thiosulfate sulfurtransferase activity compared with the starting strain.

2. The recombinant microorganism according to claim 1, wherein the starting strain is derived from a microorganism selected from the group consisting of Escherichia coli MG1655, Escherichia coli W 3110, Escherichia coli DH5a, Escherichia coli DH10B, Escherichia coli BW 2952, Escherichia coli REL 606, Corynebacterium glutamicum ATCC 13032, Corynebacterium glutamicum R, Corynebacterium glutamicum DSM20411 (former name Brevibacterium flavum), Corynebacterium glutamicum DSM 20412 (former name Brevibacterium lactofermentum), Corynebacterium glutamicum DSM 1412 (former name Brevibacterium lactofermentum), Corynebacterium efficiens YS-$314^T$ (=DSM44549), Corynebacterium glutamicum ATCC 21608, and Corynebacterium glutamicum DSM 17322.

* * * * *

SEQUENCE LISTING

<160> NUMBER OF SEQ ID NOS: 14

<210> SEQ ID NO 1
<211> LENGTH: 450
<212> TYPE: DNA
<213> ORGANISM: Saccharomyces cerevisiae

<400> SEQUENCE: 1

```
atgttcaagc atagtacagg tattctctcg aggacagttt ctgcaagatc gcctacattg      60
gtcctgagaa catttacaac gaaggctcca aagatctata cttttgacca ggtcaggaac     120
ctagtcgaac accccaatga taaaaaacta ttggtagatg taagggaacc caaggaagta     180
aaggattaca agatgccaac tacaataaat attccggtga atagtgcccc tggcgctctt     240
ggattgcccg aaaaggagtt tcacaaagtt ttccaatttg ctaaaccacc tcacgataaa     300
gaattgattt ttctttgtgc gaaaggagta agagccaaaa ctgccgaaga gttggctcga     360
tcttatgggt acgaaaacac tggtatctat cctggttcta ttactgagtg gttagctaaa     420
ggtggtgctg acgttaagcc caaaaaataa                                       450
```

```
<210> SEQ ID NO 2
<211> LENGTH: 149
<212> TYPE: PRT
<213> ORGANISM: Saccharomyces cerevisiae

<400> SEQUENCE: 2

Met Phe Lys His Ser Thr Gly Ile Leu Ser Arg Thr Val Ser Ala Arg
1               5                   10                  15

Ser Pro Thr Leu Val Leu Arg Thr Phe Thr Thr Lys Ala Pro Lys Ile
            20                  25                  30

Tyr Thr Phe Asp Gln Val Arg Asn Leu Val Glu His Pro Asn Asp Lys
        35                  40                  45

Lys Leu Leu Val Asp Val Arg Glu Pro Lys Glu Val Lys Asp Tyr Lys
    50                  55                  60

Met Pro Thr Thr Ile Asn Ile Pro Val Asn Ser Ala Pro Gly Ala Leu
65                  70                  75                  80

Gly Leu Pro Glu Lys Glu Phe His Lys Val Phe Gln Phe Ala Lys Pro
                85                  90                  95

Pro His Asp Lys Glu Leu Ile Phe Leu Cys Ala Lys Gly Val Arg Ala
            100                 105                 110

Lys Thr Ala Glu Glu Leu Ala Arg Ser Tyr Gly Tyr Glu Asn Thr Gly
        115                 120                 125

Ile Tyr Pro Gly Ser Ile Thr Glu Trp Leu Ala Lys Gly Gly Ala Asp
    130                 135                 140

Val Lys Pro Lys Lys
145

<210> SEQ ID NO 3
<211> LENGTH: 450
<212> TYPE: DNA
<213> ORGANISM: Saccharomyces cerevisiae

<400> SEQUENCE: 3
atgttcaaac acagcaccgg tattctgtct cgtacagttt cagcacgcag tccgacttta      60
gtgcttcgga cctttacaac gaaagcccct aagatctata cttttgatca ggtccgaaat     120
ctggtagaac atccaaacga caaaaagttg ctcgttgatg tgagagaacc caaagaggtc     180
aaagattaca aaatgccgac cacgataaat attccagtta actccgctcc gggagcgctg     240
ggcctacctg aaaaagagtt tcataaggta tttcagttcg caaaaccgcc tcatgacaaa     300
gaactgatct tcttatgtgc caaggggtg cgtgcgaaaa cagcagagga acttgctcgc     360
tcgtatggtt atgaaaatac aggtatttac ccaggcagca taactgagtg gctggccaaa     420
gggggagcgg atgttaaacc caaaaagtaa                                      450

<210> SEQ ID NO 4
<211> LENGTH: 450
<212> TYPE: DNA
<213> ORGANISM: Saccharomyces cerevisiae

<400> SEQUENCE: 4
atgtttaaac attccactgg cattttgtcc cgtaccgtat cagcccgttc tccgaccctt      60
gtcctgcgta ccttcactac caaagctccc aaaatctata cctttgacca ggtgcgcaac     120
ctggttgaac atccgaacga taaaaaactg ctcgtagacg tccgtgaacc gaaagaagtg     180
aaagactaca aaatgccaac tactattaat atcccggtta acagcgcgcc gggtgctctt     240
ggtctgccgg aaaaagaatt ccacaaagta ttccagttcg ctaaaccgcc gcacgacaaa     300
```

```
gaactgattt tcttatgcgc gaagggtgtg cgtgctaaaa ccgcggaaga actggctcgt    360
tcttacggtt acgaaaacac cggcattta t ccgggctcta tcaccgaatg gctggcgaaa    420
ggtggtgctg atgtgaagcc gaagaaataa                                     450

<210> SEQ ID NO 5
<211> LENGTH: 450
<212> TYPE: DNA
<213> ORGANISM: Saccharomyces cerevisiae

<400> SEQUENCE: 5
atgttcaaac actctaccgg tatcctgtct cgtaccgttt ctgcgcgttc tccgaccctg     60
gttctgcgta ccttcaccac caaagcgccg aaaatctaca ccttcgacca ggttcgtaac    120
ctggttgaac acccgaacga caaaaaactg ctggttgacg ttcgtgaacc gaaagaagtt    180
aaagactaca aaatgccgac caccatcaac atcccggtta actctgcgcc gggtgcgctg    240
ggtctgccgg aaaaagaatt ccacaaagtt ttccagttcg cgaaaccgcc gcacgacaaa    300
gaactgatct tcctgtgcgc gaaaggtgtt cgtgcgaaaa ccgcggaaga actggcgcgt    360
tcttacggtt acgaaaacac cggtatctac ccgggttcta tcaccgaatg gctggcgaaa    420
ggtggtgcgg acgttaaacc gaaaaaataa                                     450

<210> SEQ ID NO 6
<211> LENGTH: 58
<212> TYPE: DNA
<213> ORGANISM: Artificial Sequence
<220> FEATURE:
<223> OTHER INFORMATION: Based on S. cerevisiae

<400> SEQUENCE: 6
ggtaccttaa ttaagtggat tcgaggccgg ccacgagtac tattaaagag gagaaata      58

<210> SEQ ID NO 7
<211> LENGTH: 144
<212> TYPE: DNA
<213> ORGANISM: Artificial Sequence
<220> FEATURE:
<223> OTHER INFORMATION: Based on S. cerevisiae

<400> SEQUENCE: 7
taaccggctt atcggtcagt ttcacctgat ttacgtaaaa acccgcttcg gcgggttttt     60
gcttttggag gggcagaaag atgaatgact gtccacgacg ctatacccaa agaaagtttt    120
aaacgcatac cctgcaggga gctc                                          144

<210> SEQ ID NO 8
<211> LENGTH: 3010
<212> TYPE: DNA
<213> ORGANISM: Artificial Sequence
<220> FEATURE:
<223> OTHER INFORMATION: Plasmid pMA-RDL2 based on S. cerevisiae

<400> SEQUENCE: 8
ctaaattgta agcgttaata ttttgttaaa attcgcgtta aattttttgtt aaatcagctc     60 attttttaac caataggccg aaatcggcaa atcccttat aaatcaaaag aatagaccga    120
gatagggttg agtggccgct acagggcgct cccattcgcc attcaggctg cgcaactgtt    180
gggaagggcg tttcggtgcg ggcctcttcg ctattacgcc agctggcgaa agggggatgt    240
gctgcaaggc gattaagttg ggtaacgcca gggttttccc agtcacgacg ttgtaaaacg    300
acggccagtg agcgcgacgt aatacgactc actatagggc gaattggcgg aaggccgtca    360
```

```
aggcctaggc gcgccatgag ctccctgcag ggtatgcgtt taaactttct tttgggtata    420
gcgtcgtgga cagtcattca tctttctgcc cctccaaaag caaaaacccg ccgaagcggg    480
tttttacgta aatcaggtga aactgaccga taagccggtt attatttttt gggcttaacg    540
tcagcaccac ctttagctaa ccactcagta atagaaccag gatagatacc agtgttttcg    600
tacccataag atcgagccaa ctcttcggca gttttggctc ttactccttt cgcacaaaga    660
aaaatcaatt ctttatcgtg aggtggttta gcaaattgga aaactttgtg aaactccttt    720
tcgggcaatc caagagcgcc aggggcacta ttcaccggaa tatttattgt agttggcatc    780
ttgtaatcct ttacttcctt gggttccctt acatctacca atagtttttt atcattgggg    840
tgttcgacta ggttcctgac ctggtcaaaa gtatagatct ttggagcctt cgttgtaaat    900
gttctcagga ccaatgtagg cgatcttgca gaaactgtcc tcgagagaat acctgtacta    960
tgcttgaaca ttatttctcc tctttaatag tactcgtggc cggcctcgaa tccacttaat   1020
taaggtacct cttaattaac tggcctcatg ggccttccgc tcactgcccg ctttccagtc   1080
gggaaacctg tcgtgccagc tgcattaaca tggtcatagc tgtttccttg cgtattgggc   1140
gctctccgct cctcgctca ctgactcgct gcgctcggtc gttcgggtaa agcctggggt   1200
gcctaatgag caaaaggcca gcaaaaggcc aggaaccgta aaaaggccgc gttgctggcg   1260 ttttccata ggctccgccc ccctgacgag catcacaaaa atcgacgctc aagtcagagg   1320
tggcgaaacc cgacaggact ataaagatac caggcgtttc cccctggaag ctccctcgtg   1380
cgctctcctg ttccgaccct gccgcttacc ggatacctgt ccgcctttct cccttcggga   1440
agcgtggcgc tttctcatag ctcacgctgt aggtatctca gttcggtgta ggtcgttcgc   1500
tccaagctgg gctgtgtgca cgaaccccc gttcagcccg accgctgcgc cttatccggt   1560
aactatcgtc ttgagtccaa cccggtaaga cacgacttat cgccactggc agcagccact   1620
ggtaacagga ttagcagagc gaggtatgta ggcggtgcta cagagttctt gaagtggtgg   1680
cctaactacg gctacactag aagaacagta tttggtatct gcgctctgct gaagccagtt   1740
accttcggaa aaagagttgg tagctcttga tccggcaaac aaaccaccgc tggtagcggt   1800
ggtttttttg tttgcaagca gcagattacg cgcagaaaaa aaggatctca agaagatcct   1860
ttgatctttt ctacggggtc tgacgctcag tggaacgaaa actcacgtta agggattttg   1920
gtcatgagat tatcaaaaag gatcttcacc tagatccttt taaattaaaa atgaagtttt   1980
aaatcaatct aaagtatata tgagtaaact tggtctgaca gttaccaatg cttaatcagt   2040
gaggcaccta tctcagcgat ctgtctattt cgttcatcca tagttgcctg actccccgtc   2100
gtgtagataa ctacgatacg ggagggctta ccatctggcc ccagtgctgc aatgataccg   2160
cgagaaccac gctcaccggc tccagattta tcagcaataa accagccagc cggaagggcc   2220
gagcgcagaa gtggtcctgc aactttatcc gcctccatcc agtctattaa ttgttgccgg   2280
gaagctagag taagtagttc gccagttaat agtttgcgca acgttgttgc cattgctaca   2340
ggcatcgtgg tgtcacgctc gtcgtttggt atggcttcat tcagctccgg ttcccaacga   2400
tcaaggcgag ttacatgatc ccccatgttg tgcaaaaaag cggttagctc cttcggtcct   2460
ccgatcgttg tcagaagtaa gttggccgca gtgttatcac tcatggttat ggcagcactg   2520
cataattctc ttactgtcat gccatccgta agatgctttt ctgtgactgg tgagtactca   2580
accaagtcat tctgagaata gtgtatgcgg cgaccgagtt gctcttgccc ggcgtcaata   2640
cgggataata ccgcgccaca tagcagaact ttaaaagtgc tcatcattgg aaaacgttct   2700
```

-continued

```
tcggggcgaa aactctcaag gatcttaccg ctgttgagat ccagttcgat gtaacccact    2760
cgtgcaccca actgatcttc agcatctttt actttcacca gcgtttctgg gtgagcaaaa    2820
acaggaaggc aaaatgccgc aaaaaaggga ataagggcga cacggaaatg ttgaatactc    2880
atactcttcc tttttcaata ttattgaagc atttatcagg gttattgtct catgagcgga    2940
tacatatttg aatgtattta gaaaataaac aaatagggg ttccgcgcac atttccccga    3000
aaagtgccac                                                            3010
```

<210> SEQ ID NO 9
<211> LENGTH: 20
<212> TYPE: DNA
<213> ORGANISM: Artificial Sequence
<220> FEATURE:
<223> OTHER INFORMATION: pECf primer based on E. coli

<400> SEQUENCE: 9
tactgccgcc aggcaaattc                                                 20

<210> SEQ ID NO 10
<211> LENGTH: 20
<212> TYPE: DNA
<213> ORGANISM: Artificial Sequence
<220> FEATURE:
<223> OTHER INFORMATION: pECr primer based on E. coli

<400> SEQUENCE: 10
tttgcgccga catcataacg                                                 20

<210> SEQ ID NO 11
<211> LENGTH: 55
<212> TYPE: DNA
<213> ORGANISM: Artificial Sequence
<220> FEATURE:
<223> OTHER INFORMATION: RDL2-t4-f primer based on E. coli

<400> SEQUENCE: 11
aggacagtcg acggtaccgc aagcttcggc ttcgcactgg aaagcgggca gtgag          55

<210> SEQ ID NO 12
<211> LENGTH: 20
<212> TYPE: DNA
<213> ORGANISM: Artificial Sequence
<220> FEATURE:
<223> OTHER INFORMATION: RDL2-r primer based on E. coli

<400> SEQUENCE: 12
agcgcgacgt aatacgactc                                                 20

<210> SEQ ID NO 13
<211> LENGTH: 20
<212> TYPE: DNA
<213> ORGANISM: Artificial Sequence
<220> FEATURE:
<223> OTHER INFORMATION: pME-RDL2-Seqf primer based on E. coli

<400> SEQUENCE: 13
atgtggaagc cggactagac                                                 20

<210> SEQ ID NO 14
<211> LENGTH: 20
<212> TYPE: DNA

```
<213> ORGANISM: Artificial Sequence
<220> FEATURE:
<223> OTHER INFORMATION: pME-RDL2-Seqr primer based on E. coli

<400> SEQUENCE: 14
tcggattatc ccgtgacagg                                              20
```